United States Patent [19]

von Borstel et al.

[11] Patent Number: 5,583,117

[45] Date of Patent: * Dec. 10, 1996

[54] ACYLATED URIDINE AND CYTIDINE FOR ELEVATING TISSUE URIDINE AND CYTIDINE

[75] Inventors: Reid von Borstel, Kensington; Michael K. Bamat, Chevy Chase, both of Md.

[73] Assignee: Pro-Neuron, Inc., Rockville, Md.

[ * ] Notice: The term of this patent shall not extend beyond the expiration date of Pat. No. 5,470,838.

[21] Appl. No.: 140,475

[22] Filed: Oct. 25, 1993

Related U.S. Application Data

[62] Division of Ser. No. 737,913, Jul. 29, 1991, abandoned, which is a continuation of Ser. No. 115,929, Oct. 28, 1987, abandoned.

[51] Int. Cl.$^6$ .................. A61K 31/70; C07H 19/067
[52] U.S. Cl. .................. 514/50; 514/49; 536/28.5; 536/28.53
[58] Field of Search .................. 514/49, 50; 536/28.5, 536/28.53

[56] References Cited

U.S. PATENT DOCUMENTS

| | | | |
|---|---|---|---|
| 3,585,188 | 6/1971 | Ryuji | 536/28.53 |
| 3,847,898 | 11/1974 | Kelly | 536/28.51 |
| 3,868,451 | 2/1975 | Stein et al. | 514/46 |
| 3,894,000 | 7/1975 | Wechter et al. | 536/23 |
| 3,975,367 | 8/1975 | Gish et al. | 530/322 |
| 3,991,045 | 11/1976 | Ichida et al. | 536/28.51 |
| 4,022,963 | 5/1977 | Deutsch | 536/28.3 |
| 4,868,162 | 9/1989 | Kawaguchi et al. | 514/50 |

FOREIGN PATENT DOCUMENTS

| | | |
|---|---|---|
| 0056265 | 1/1982 | European Pat. Off. . |
| 0178217 | 4/1986 | European Pat. Off. . |
| 0232192 | 5/1987 | European Pat. Off. . |
| 2147094 | 4/1973 | Germany . |
| 51-019779 | 2/1976 | Japan . |
| 0023085 | 2/1977 | Japan . |
| 58-49315 | 2/1980 | Japan . |
| 81-035196 | 8/1981 | Japan . |
| 57-91995 | 6/1982 | Japan . |
| 55-24150 | 3/1983 | Japan . |
| 0049315 | 3/1983 | Japan . |
| 60-174797 | 2/1984 | Japan . |
| 1297398 | 11/1972 | United Kingdom . |

OTHER PUBLICATIONS

Lim et al. Antimicroaial Agents and Chemotherapy 31: 998–1001, 1987.
Martin et al. J. Pharmaceutical Sciences 76(2): 180–184, 1987.
Rosowsky et al. Cancer Treatment Reports 85(1–2): 93–99, 1981.
Ensminger et al. Biochem Pharmacol. 28: 1541–1545, 1979.
Rajabalee, the Chemical Abstracts, 74:112368K (1971).
Aussedat et al, the Chemical Abstracts, 101:149186b (1984).
Bushma et al, the Chemical Abstracts, 92:105249r (1980).
Kypson et al, the Chemical Abstracts, 87:194780u (1977).
Lortet et al, the Chemical Abstracts, 105:112608y (1986).
Hackh's Chemical Dictionary 3rd ed. Julius Grant, ed. pp. 44, 45, 332, 333, 1944.
Aussedat, *Cardiovasc. Res.* 17:145–151 (1983).
Aussedat et al, *Mol. Physiol.*, 6:247–256 (1984).
Aussedat et al, *J. Physiol.* 78:331–336 (1982).
Buckley et al, *Circ. Res.* 7:847–867 (1959).
Kuznetsova et al, *Farmakol.–Toksikol* 2:170–173 ((1981).
Kypson et al, *J. Mol. Cell. cardiol.* 10:545–565 (1978).
Lortet et al, *Basic Res. Cardiol.* 81:303–310 (1986).
Meerson et al, *Kardiologiya* 25:91–93 (1985).
Rossi et al, *European Heart Journal*, 5:155–162 (1984).
Eliseev et al, *Khim–Farm. Zh.*, 19:694–696 (1985).
Williams et al, *Aust. N.Z. J. Med.*, 6:Supp. 2, 60–71 (1976).
Swain et al, *P.N.A.S. (USA)* 79:655–659 (1982).
Kypson et al, *Biochem. Pharmacol.* 26:1585–1591 (1977).
Pastoris et al, *Pharm. Ed. Sci.* 40:442–453 (1985).
Kypson et al, *J. Pharm. Exp. Ther.* 199:565–574 (1976).
Gasser et al, *Science* 213:777–778 (1981).
Klubes et al, *Cancer Chemother. Pharmacol.* 17:236–240 (1986).
Bucher et al, *Biochem. Phys. Acta*, 174:491–502 (1969).
Bushma et al, *Bull. Exp. Biol. Med.* 88:1480–1483 (1980).
Chernukh et al, *Bull Exp. Biol. Med.* 70:1112–1114 (1970).
Diamondstone et al, *Biochim. Biophys. Acta* 57:583–587 (1962).
Elrick et al, *Metabolism*, 11:46–55 (1962).
Yamada et al, *J. Biol Chem.* 243:1649–1655 (1968).
Shah et al, *J. Anim. Morphol. Physiol.* 25:193–200 (1978).
Shah et al, *J. Anim. Morphol. Physiol.* 21:132–139 (1974).
Songu et al, *Metabolism* 30:119–122 (1981).
Germanyuk et al, *Farmakol. Toksikol.* 50–52 (1979).
Trovarelli et al, *Neurochemical Research*, 9:73–79 (1984).
Dwivedi et al, *Toxicol. Appl. Pharmacol.*, 31:452 (1978).
Geiger et al, *J. Neurochem.*, 1:93 (1956).
Sepe, *Minerva Medica*, 61:5934 (1970).
Jann et al, *Minerva Medica*, 60:2092 (1969).
Beranek, et al, *Collection Czechslovak Chem. Commun.*, 42:366–369 (1977).
Sasaki et al, *Chem. Pharm. Bull.*, 15:894–896 (1967).
Samoileva et al, *Bull. Acad. Sci. USSR Div. Chem. Sci.* 30:1306–1310 (1981).
Watanabe et al, *Angew, Chem.* 78:589 (1986).
Reese et al, *Tetrahedron Letters* 29:2459–2465 (1965).

*Primary Examiner*—Gary L. Kunz
*Attorney, Agent, or Firm*—Nixon & Vanderhye P.C.

[57] ABSTRACT

General methods for delivering exogenous cytidine or uridine to the tissue of an animal comprising the administration of acylated cytidine or acylated uridine, respectively, are disclosed. Methods of treating myocardial infarction and cardiac insufficiency comprising the administration of acylated cytidine or acylated uridine, are also disclosed.

20 Claims, 5 Drawing Sheets

ACYLATED URIDINE AND CYTIDINE FOR ELEVATING TISSUE URIDINE AND CYTIDINE

This is a divisional of application Ser. No. 07/737,913, filed Jul. 29, 1991 which is a continuation of Ser. No. 07/115,929 filed Oct. 28, 1987, now abandoned.

FIELD OF THE INVENTION

This invention relates generally to acyl derivatives of cytidine and uridine and to the use of those derivatives to enhance the delivery of exogenous ribonucleosides to animal tissue. More specifically, this invention relates to the acyl derivatives of cytidine and uridine, and the uses of those novel derivatives to increase the bioavailability of these ribonucleosides to animal tissue and thereby to support cellular metabolic functions. Even more specifically, this invention relates to the use of the novel acyl derivatives to treat or prevent a variety of physiological and pathological conditions, including treatment of liver disease or damage, cerebrovascular disorders, bone fractures, respiratory distress syndromes, senile dementias, cardiac damage, and other clinical conditions.

BACKGROUND OF THE INVENTION

There are many physiological and pathological conditions of animal tissue where the supply of exogenous ribonucleosides may have useful therapeutic applications. In a number of physiological and pathological conditions, the administration to an animal of RNA, nucleotides, or individual or mixtures of nucleosides, has been shown to improve the natural repair processes of the affected cells.

There are many important metabolic reactions that are usually functionally subsaturated and limited by availability of either substrates or cofactors. Such rate-limiting compounds may be either nutritionally essential or synthesized de novo in the body. Under conditions of tissue trauma, infection or adaptation to physiological demand, particularly when cellular repair or regeneration processes are activated, the optimum nutritional, biochemical, or hormonal environment for promoting such repair may be quite different from the requirements for normal cell and tissue function. In such cases, therapeutic benefit may be derived by providing appropriate conditionally essential nutrients, such as ribonucleosides or metabolites which may be required in quantities not usually available from a normal diet.

The therapeutic potential for this strategy of directly supporting the metabolic function of damaged or diseased tissues has not been realized in contemporary medical practice. For example, the routine treatment of cardiac insufficiency involves the use of agents which elicit increases in cardiac work output (e.g., cardiac glycosides), but which do not support or improve the actual functional capacity of myocardial metabolism. Similarly, in the cases of liver disease or damage, cerebrovascular disorders, bone fractures, respiratory distress syndrome, senile dementias, and most other clinical conditions, contemporary treatments generally do not include intentional methods for improving the capacity of tissues to undergo repair or compensatory metabolic or structural adaptations.

At the cellular level of organization, there are specific metabolic responses to trauma that are involved, in a variety of tissues, in the processes of tissue repair, regeneration, or adaptation to altered functional demand. Most processes of tissue damage and repair are accompanied by a substantial increase in the activity of the hexose monophosphate pathway of glucose metabolism.

The hexose monophosphate pathway is the route of formation for the penrose sugars (e.g., ribose) which are necessary for nucleotide and nucleic acid synthesis. The availability of ribose is rate limiting for nucleotide synthesis under most physiological or pathological conditions. Rapid production of nucleotides for the synthesis of nucleic acids and nucleotide-derived cofactors (such as cytidine di-phosphocholine or uridine di-phosphoglucose (UDPG)) is essential for the processes of tissue repair and cellular proliferation. Even though nucleotides are synthesized de novo from simpler nutrients, so that there is not an absolute dietary requirement for direct nucleotide precursors, many tissues may not have optimal capacity for nucleotide synthesis particularly during tissue repair or cellular proliferation.

It is possible to bypass the limited capacity of the hexose monophosphate pathway by providing preformed ribonucleosides directly to tissues where they are incorporated in the nucleotide pools via the "salvage" pathways of nucleotide synthesis. It is also possible that pyrimidine ribonucleosides may exert therapeutic influences through mechanisms unrelated to the support of nucleotide biosynthesis.

The effects of the administration of pyrimidine nucleosides, and in particular, uridine and cytidine, on a variety of physiological and pathological conditions in experimental animals and to some extent in humans have been extensively studied. These are summarized below.

(1) Heart

In isolated rat hearts subjected to low-flow ischemia, reperfusion with uridine induced restoration of myocardial ATP levels, total adenine nucleotide content, uridine nucleotide levels, and glycogen content. Ischemia was reported to produce a breakdown of creatinine phosphate, ATP, uridine nucleotides and glycogen. Aussedat, J., *Cardiovasc. Res.* 17:145–151 (1983).

In a related study, perfusion of isolated rat hearts with uridine resulted in a concentration-dependent elevation of myocardial uracil nucleotide content. Following low-flow ischemia, the rate of incorporation of uridine was increased twofold. Aussedat, J., et al., *Mol. Physiol.* 6:247–256 (1984).

In another study, isoproterenol was administered to rats which depleted cardiac glycogen stores and reduced myocardial UTP and UDP-glucose levels. Despite the spontaneous restoration of myocardial UTP levels, UDP-glucose concentrations remained depressed unless uridine or ribose were administered. Intravenous infusion of ribose or uridine resulted in a restoration of myocardial glycogen. Thus, there may be compartmentation of uridine nucleotides in the heart, with the pools being fed differentially by the salvage or de novo pathways of pyrimidine synthesis. Aussedat, J., et al., *J. Physiol.* 78:331–336 (1982).

The effects of nucleosides on acute left ventricular failure in isolated dog heart was studied by Buckley, N. M., et al., *Circ. Res* 7:847–867 (1959). Left ventricular failure was induced in isolated dog hearts by increasing aorta pressure. In this model, guanosine, inosine, uridine and thymidine were found to be positive inotropic agents, while cytidine and adenosine were negatively inotropic.

Sodium uridine monophosphate (UMP) and potassium orotate were found to increase the animal's resistance to subsequent adrenalin-induced myocardial necrosis. These compounds reduced mortality and improved myocardial function as assessed by ECG readings, biochemical findings, and relative heart weight. Administration of UMP exerted a more pronounced prophylactic effect than did potassium orotate. Kuznetsova, L. V., et al., *Farmakol.-Toksikol* 2:170–173 (1981).

In a study on the effects of hypoxia in isolated rabbit hearts, myocardial performance declined while glucose uptake with glycolysis, glycogenolysis and breakdown of adenine nucleotides were reportedly increased. Administration of uridine increased myocardial performance, glucose uptake and glycolysis and also diminished the disappearance of glycogen and adenine nucleotides from hypoxic hearts. Uridine also increased glucose uptake, glycolysis, levels of ATP and glycogen, as well as myocardial performance in propranolol-treated hearts. Kypson, J., et al., *J. Mol. Cell. Cardiol.* 10:545–565 (1978).

In a study of pyrimidine nucleotide synthesis from exogenous cytidine in the isolated rat heart, myocardial cytosine nucleotide levels were significantly increased by a 30 minute supply of cytidine. Most of the cytidine was recovered as part of cytosine nucleotides and uracil nucleotides. Very little of the cytidine that was taken up was converted into uridine nucleotides. These results suggest that the uptake of cytidine can play an important part in myocardial cytosine nucleotide metabolism. Lortet, S., et al., *Basic Res. Cardiol.* 81:303–310 (1986).

In another study, myocardial fatigue was produced by repeated, brief ligations of the ascending aorta. Administration of a mixture of uridine and inosine after the fifth such ligation temporarily stopped the development of fatigue in the myocardium. Pretreatment with an undisclosed amount of uridine prevented the decrease in maximal pressure upon aortic ligation that is observed 2 hours after aortic stenosis. Meerson, F. C., In: *Tr. Vseross. S'ezda Ter.*, Myasnikov, A. L. (ed.), Meditsina (publisher), Moscow, p. 27–32 (1966).

In another study, the use of glucose and uridine to control contractability and extensibility disturbances in the non-ischematized compartments of the heart in myocardial infarction were studied. The deficits in contractability and extensibility were reported to be probably due to sustained sympathetic nervous activity. The administration of glucose or uridine restored contractability and extensibility of the atrial tissue in vitro. Meerson, F. Z., et al., *Kardiologiya* 25:91–93 (1985).

In a study of experimental cardiac hypertrophy in rats, both ribosomal RNA and uridine nucleotide synthesis were found to be elevated. The authors suggest that the increase in uracil nucleotide synthesis is an adaptive change in response to increased requirements for RNA precursors. Rossi, A., et al., *European Heart Journal* 5:155–162 (1984).

Despite the above results which were observed in isolated hearts, or in situ organ preparations, the administration of uridine to intact (i.e., alive and free-running) animals has not been demonstrated to be beneficial. Thus, while Eliseev, V. V., et al., *Khim-Farm. Zh.* 19:694–696 (1985) (CA 103:82603k) disclose that uridine-5'-monophosphate has a protective effect on rats with adrenalin-induced myocardial dystrophy, uridine was found to be relatively ineffective. Moreover, Williams, J. F., et al., *Aust. N.Z. J. Med.* 6:Supp. 2, 60–71 (1976), disclose that with rats developing hypertrophy of the heart, there was no difference between rats which were treated with uridine compared with controls. Thus, except for rats which received continuous infusion of uridine (Aussedat et al., supra), no beneficial effect on pathology related to the heart has been demonstrated with uridine administration.

In another study, the changes in nucleotide levels and metabolism, observed in human patients with coronary artery disease or left ventricular hypertrophy, were reported to be similar to the changes found in experimental models of these disorders in laboratory animals. Swain, J. L., et al., *P.N.A.S. (USA)* 79:655–659 (1982).

(2) Muscles

Exposure to uridine has also been found to enhance glucose uptake and glycogen synthesis in both skeletal and cardiac muscle. Kypson, J., et al., *Bioch. Pharmacol.* 26:1585–1591 (1977). Uridine and inosine were found to stimulate glucose uptake in isolated rat diaphragm muscle. However, only uridine increased glycogen synthesis. Both nucleosides inhibited lipolysis in adipose tissue. Kypson, J., et al., *J. Pharm. Exp. Ther.* 199:565–574 (1976). Thus, administration of uridine is effective in enhancing glucose uptake and glycogen synthesis in skeletal muscle.

Pastoris, O., et al., *Pharm. Ed. Sci.* 40:442–453 (1985), disclose administration of cytidine to rats with experimentally induced hypoxia in the skeletal muscles. Administration of cytidine to hypoxic rats was found to affect the muscular concentrations of Krebs cycle intermediates. However, uridine itself is catabolized to a large extent, rather than taken up and utilized for nucleotide synthesis. Gasser, T., et al., *Science* 213:777–778 (1981), disclose that the isolated, perfused rat liver degrades more than 90% of infused uridine in a single passage. Much of the uridine released by the liver in the portal vein is from degradation of liver nucleotides synthesized de novo rather than from arterial uridine. This accounts for the poor utilization of administered uridine in peripheral tissues.

(3) Plasma

For example, Klubes, P., et al., *Cancer Chemother. Pharmacol.* 17:236–240 (1986), disclose that after oral administration of 350 (mg/kg of uridine in mice, plasma levels of uridine were not perturbed. In contrast, plasma levels of uracil, a catabolite of uridine, peaked at 50 micro then declined and returned to normal after 4 h. Elevation of plasma uridine levels was observed only after oral administration of high doses of uridine (3500 mg/kg). However, such doses would be much too high for an adult human since they would amount to about 200 g/dose.

(4) Liver

In studies of rat liver regeneration after partial hepatectomy, free pyrimidine nucleotide pools were found to increase in size by about 50%, as does the RNA content and the rate of RNA synthesis. Bucher, N. L. R., et al., *Bioch. Biophys. Acta* 174:491–502 (1969).

Administration of cytidine and uridine has also been found to be effective in enhancing the regeneration of the liver in rats poisoned with carbon tetrachloride. Bushma, M. I., et al., *Bull. Exp. Biol. Med.* 88:1480–1483 (1980).

There have been a number of reports relating to the therapeutic administration of nucleotides and RNA. The beneficial effects of RNA or nucleotides are probably due to their being broken down to individual ribonucleosides by phosphorylases. For example, injection of cytoplasmic RNA from the rat liver into mice during chronic poisoning with $CCl_4$ reduced the mortality among the animals. Moreover, the number of foci of necrosis were reduced and the number of interlobular connective tissue fibers in the liver were increased. An increase in the mitotic activity of the liver cells was also observed. Chernukh, A. M., et al., *Bull. Exp. Biol. Med.* 70: 1112–1114 (1970).

Administration of RNA, mixed nucleotides, or hydrocortisone, either alone or in various combinations, was found to increase tyrosine-alpha-ketoglutarate activity in rat liver. Administration of RNA or nucleotides elevated enzymatic activity beyond the level attained after hydrocortisone administration alone. The authors speculated that the RNA or nucleotides may act via two mechanisms: first, a nonspecific stress effect, mediated through stimulation of adrenal steroid release, or secondly, through provision of limiting substrates for RNA synthesis. Diamondstone, T. I., et al., *Biochim. Biophys. Acta* 57:583–587 (1962). In a study on human patients with hepatic cirrhosis, administration of cytidine and uridine improved insulin sensitivity in the cirrhotic patient, but had no effect on insulin sensitivity in patients without liver disease. Ehrlich, H., et al., *Metabolism* 11:46–55 (1962).

Yamada, E., *J. Biol. Chem.* 243:1649–1655 (1968), discloses the effect of cytidine injection into rats on pyrimidine nucleoside phosphorylases in regenerating rat liver. The specific activity of liver homogenates was found to be increased.

In a study of wound healing and repair in the liver, a rapid, sustained increase in RNA content of cells at the border of experimentally induced wounds was observed. DNA concentrations in the wound area began to rise on the third day after wounding and continued to rise till the 10th day. The diabetic rat liver, in contrast, showed poor RNA and DNA contents. Increases in the tissue content of RNA and DNA around the wound site were delayed and strongly depressed relative to nondiabetic livers. The failure of RNA synthesis, which gives rise to poor wound healing in the diabetic liver, was attributed to deficient activity of the hexose monophosphate pathway of glucose metabolism as observed in diabetics. Shah, R. V., et al., *J. Anim. Morphol. Physiol.* 25:193–200 (1978); Shah, R. V., et al., *J. Anim. Morphol. Physiol.* 21:132–139 (1974).

In another study, the availability of UDPG was found to be rate-limiting for hepatic glycogen synthesis under some conditions. When hepatocytes were incubated with uridine, there was an increase in the incorporation of glucose into glycogen and tissue uridine nucleotide pools were expanded. When uridine was omitted from the incubation mixture, levels of UTP and UDP-glucose dropped markedly during a 1 hour incubation. Songu, E., et al., *Metabolism* 30:119–122 (1981). In a study of patients with alcoholic hepatitis, a beneficial effect of uridine-diphosphoglucose, when administered intramuscularly or intravenously, was found in biochemical indices as well as physiological and psychological symptoms. Thus, pyrimidine nucleosides are effective in treatment of pathology of the liver.

(5) Bone

Reparation of rat femur fractures was found to depend considerably on the activity of the pentose phosphate shunt at the initial periods of healing. In the healing of the rat femur fracture, activity of glucose-6-phosphate dehydrogenase and total content of nucleic acids were increased in the callus, reaching the maximum value within 1 week after the fracture. Vlasov, B. Y., et al., *Vopr. Med. Khim.* 30:46–47 (1984).

(6) Diabetes

Nucleosides are also useful for the treatment of diabetes. In experimental diabetes, RNA synthesis is reduced in a number of tissues. Administration of oral sodium ribonucleate was found to increase the rate of RNA biosynthesis in tissues of diabetic rats. Germanyuk, Y. L., et al., *Farmakol. Toksikol.* 50–52 (1979). This effect is probably a result of hydrolysis of the administered RNA to give individual ribonucleotides and/or ribonucleosides.

Ribonucleic acids have also been used for treatment of diabetes in rabbits in combination with injections of insulin. RNA plus insulin increased blood purine nucleotides and activated RBC enzymes of purine metabolism (ATPase, 5'-nucleotidease and 3'-nucleotidease) to a greater extent than did insulin alone. The diabetic rabbits treated with RNA plus insulin also weighed more than those receiving insulin alone. Germanyuk, Y. L., et al., *Pat. Fiziol.* 3:44–47 (1969). The failure of RNA synthesis in the diabetic rat liver has been attributed to the deficient activity of the hexose monophosphate pathway of glucose metabolism in diabetes. Shah, R. V., et al., *J. Anim. Morphol. Physiol.* 25:193–200 (1978). In addition, protein synthesis in the diabetic rat liver has been reported to be depressed. This is reportedly due to the reduced availability of messenger RNA rather than defects in ribosomal function per se or cofactor availability. Tragl, K. H., et al., *Diabetes* 20:27–32 (1971). Thus, administration of pyrimidine nucleosides to bypass the limitations of the hexose monophosphate pathway has the effect of increasing the rate of wound healing in diabetic patients.

(7) Phospholipid Biosynthesis

Cytidine nucleotides have been implicated in phospholipid biosynthesis. For example, Trovarelli, G., et al., *Neurochemical Research* 9:73–79 (1984), disclose that upon the intraventricular administration of cytidine into the brain of rats, a measurable increase in the concentrations of all the nucleotides, CDP-choline, CDP-ethanolamine, and CMP occurred. The authors state that the low concentration of free cytidine nucleotides in nervous tissue likely limits the rate of phospholipid biosynthesis.

(8) Brain

Administration of cytidine and uridine has also been reported to be effective in the treatment of various neurological conditions in animals. For example, Dwivedi et al., *Toxicol. Appl. Pharmacol.* 31:452 (1978) disclose that uridine, administered by intraperitoneal injection in mice, is an effective anticonvulsant, providing strong protection against experimentally-induced seizures.

Geiger et al., *J. Neurochem* 1:93 (1956) disclose that the functional condition of circulation-isolated cat brains perfused with washed bovine erythrocytes suspended in physiological saline remained normal for only about 1 hour. If either the animal's liver was included in the perfusion circuit, or cytidine and uridine were added to the perfusate, the functional condition of the brain remained good for at least 4 to 5 hours. The cytidine and uridine tended to normalize cerebral carbohydrate and phospholipid metabolism. The authors suggest that the brain is dependent upon a steady supply of cytidine and uridine, which are perhaps normally supplied by the liver.

Sepe, *Minerva Medica* 61:5934 (1970), disclose the effect of daily intramuscular injections of cytidine and uridine in neurological patients, most suffering from cerebrovascular disorders. Beneficial results were obtained, particularly with respect to restoration of motor function, and in improving recovery after cranial trauma. No undesirable side effects were observed.

Jann et al., *Minerva Medica* 60:2092 (1969) disclose a study of patients with a variety of neurological disorders which were treated daily with intramuscular injections of cytidine and uridine. Beneficial effects were observed, particularly in cerebrovascular disorders involving motor function and mental efficiency. No undesirable side effects were observed.

Monticone et al., *Minerva Medica* 57:4348 (1966), disclose a study of patients with a variety of encephalopathies which were treated with daily intramuscular injections of cytidine and uridine. Beneficial effects were found in most patients, particularly those with cerebrovascular disorders or multiple sclerosis. No undesirable side effects were observed.

One method that has heretofore been used, in effect, to introduce cytidine equivalents into patients is the administration of cytidine-diphosphocholine (CDP-choline). Cytidine-diphosphocholine, an intermediate in the biosynthesis of phosphatidyl choline (lecithin) is used therapeutically in Europe and Japan (under such names as Somazina, Nicholin, and Citicholine) for treating a variety of disorders. Therapeutic efficacy has been documented in central nervous system pathologies including brain edema, cranial trauma, cerebral ischemia, chronic cerebrovascular diseases, and Parkinson's disease. The mechanism underlying the pharmacological actions of this compound is believed to involve support of phospholipid synthesis, restoration of the biochemical "energy charge" of the brain, or a possible effect on neurotransmitter (particularly dopamine) function.

Examination of the fate of CDP-choline following its administration to animals or humans indicates that this compound is very rapidly degraded, yielding cytidine, choline, and phosphate. After oral administration, no intact CDP-choline enters the circulation, although plasma cytidine and choline concentrations rise. After intravenous injection, breakdown to cytidine and choline occurs within about 30 seconds. Therefore, it is difficult to attribute the therapeutic effects of exogenous CDP-choline to the entry of this compound directly into cellular metabolism.

Therapeutic benefits in cerebral pathologies similar to those obtained with CDP-choline have been achieved following administration of cytidine and uridine to humans and experimental animals. Therefore, CDP-choline appears to serve merely as an inefficient, expensive "prodrug" for cytidine, use of which perhaps hinders rather than enhances the transport of cytidine to target tissues, compared to administration of cytidine itself. Administration of choline by itself does not result in the therapeutic benefits obtained after administration of either cytidine or CDP-choline.

Cytidine, however, is not very readily taken up by the brain, although quantities sufficient to produce therapeutic effects do enter the brain after administration of CDP-choline or cytidine, particularly after parenteral injection. It would thus be advantageous to develop methods for delivering cytidine to the brain that are less expensive and/or more efficient than administration of CDP-choline or cytidine itself.

Uridine-diphosphoglucose, uridine-diphosphoglucuronic acid, and uridine diphosphate also have been shown to improve certain aspects of liver function. Since such phosphorylated compounds, as well as CDP-choline, must in general be dephosphorylated before they will enter cells, administration of uridine, or derivatives of uridine, should represent a substantial improvement, in terms of both efficiency and cost, over the use of the phosphorylated pyrimidine derivatives.

Certain uridine and cytidine derivatives are known, per se. Honjo, et al., in British Patent No. 1,297,398, describe $N^4O^{2'},O^{3'},O^{5'}$-tetraacylcytidines and a process for their preparation. The acyl substituents are those derived from fatty acids having from three to eighteen carbon atoms. The compounds are said to show pharmacological action such as central nervous system activating effects and show results in the treatment of disturbance of consciousness or neuropsychiatric symptoms such as are due to head injuries, cerebralvascular disturbance, or cerebral operation.

Beranek, et al., *Collection Czechslovak Chem. Commun.* (vol. 42, 1977), p. 366–369, describe the preparation of 2',3',5'-tri-O-acetylcytidine hydrochloride from cytidine by reaction with acetyl chloride in acetic acid.

Sasaki, et al., *Chem. Pharm. Bull.* (vol. 15, 1967), describe the acetylation of cytidine with acetic anhydride to form $N^4$-acetylcytidine, 5'-O-acetylcytidine and $N^4$5'-O-diacetylcytidine, among other compounds.

U.S. Pat. No. 4,022,963 to Deutsch, describes methods for acetylating all of the hydroxyl groups in the sugar portion of nucleosides which include uridine, by a process including the addition of excess acetic anhydride.

Samoileva, et al., *Bull. Acad. Sci. USSR Div. Chem. Sci.* Vol. 30, 1981, pp. 1306–1310 disclose a method for synthesizing aminoacyl or peptidyl derivatives of cytidine or cytidine monophosphate using insoluble polymeric N-hydroxysuccinimide. $N^4$-BOC-alanyl cytidine was prepared. The aminoacyl derivatives of cytidine were synthesided as probes for studying the function of nucleases.

Japanese Patent Publications Nos. 51019779 and 81035196 assigned to Asahi Chemical Ind. KK describe methods for preparing $N^4$-acyl-cytidines by reacting cytidine with acid anhydrides derived from fatty acids containing 5 to 46 carbon atoms. The products are said to be lipophilic ultra-violet absorbing agents and are also useful as starting compounds in the preparation of anti-tumor agents.

Watanabe, et al., *Angew. Chem.*, Vol. 78, 1986, p. 589 describe methods for selective acylation of the $N^4$-amino group of cytidine wherein methanol is used as a solvent and acid anhydride as acylating agent. Compounds prepared were $N^4$-acetyl-, $N^4$-benzoyl-, and $N^4$-butyryl-cytidine.

Rees, et al., *Tetrahedron Letters*, Vol. 29, 1965, p. 2459–2465 disclose methods for selective acylation of the 2' position on the ribose moiety of ribonucleosides. Uridine derivatives were prepared including 2'-O-acetyluridine, 2'-O-benzyluridine, and 2',5'-di-O-acytluridine and other derivatives. The compounds were prepared as intermediates in oligo ribonucleotide synthesis.

OBJECTS OF THE INVENTION

While certain acylated derivatives of uridine and cytidine are known and while the studies summarized above demonstrate that the presence of uridine and cytidine is important to the amelioration of a variety of physiological and pathological conditions and that methods for enhancing the delivery of uridine and cytidine to animal tissue may provide an important source of those nucleosides, the art has heretofore failed to provide methods for introducing uridine and cytidine into animal tissue at rates sufficiently high to reliably assist in metabolic processes.

It is thus a primary object of this invention to identify pharmaceutically acceptable compounds which can be used efficiently to deliver pharmaceutically effective amounts of uridine and/or cytidine or their respective derivatives to animal tissue.

It is still a further object of this invention to provide a family of uridine and cytidine derivatives which can be effectively administered orally or parenterally and which have no untoward pharmaceutical effects.

It is still a further and related object of this invention to provide a family of uridine and cytidine derivatives which, when administered to an animal, preferably humans, substantially improves the bioavailability of cytidine and uridine by enhancing the transport of those nucleosides across the gastrointestinal tract, the blood-brain barrier, and other biological membranes and which allow sustained delivery of high levels of these ribonucleosides to animal tissues.

It is still a further and more specific object of this invention to provide a family of cytidine and uridine derivatives for the treatment of a variety of heart, muscle, plasma, liver, bone, diabetic, and neurological conditions.

These and other objects of the invention are achieved through the administration of novel acyl derivatives of uridine and cytidine. Broadly, the acyl derivatives of uridine comprise compounds having the formula

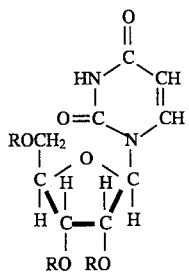
(I)

wherein R is hydrogen or an acyl radical of a metabolite, with the provisos that at least one R is not hydrogen and R is not acetyl, or the pharmaceutically acceptable salt thereof.

The preferred acyl derivatives of uridine are those having the formula

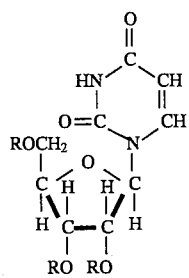
(I)

wherein R is H or an acyl group derived from a carboxylic acid selected from one or more of the group consisting of acetic acid, glycolic acid, pyruvic acid, lactic acid, enolpyruvic acid, an amino acid, a fatty acid other than acetic acid, lipoic acid, pantothenic acid, succinic acid, fumaric acid, adipic acid, acetoacetic acid, p-aminobenzoic acid, betahydroxybutyric acid, orotic acid, and creatin, with the provisos that at least one R is not hydrogen and not all of said R substituents are acetyl, or the pharmaceutically acceptable salt thereof.

The objects of the invention are also achieved with acyl derivatives of uridine comprising compounds having the formula

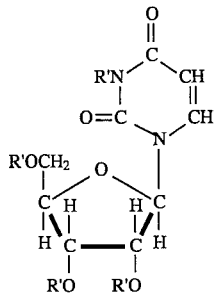
(II)

wherein R' is hydrogen or an acyl radical of a metabolite other than $CH_3CHO$—, with the proviso that at least one R' is not hydrogen, or the pharmaceutically acceptable salt thereof.

Preferably, the compounds having formula (II) are those wherein R' is H or an acyl group derived from a carboxylic acid selected from one or more of the group consisting of a fatty acid, glycolic acid, pyruvic acid, lactic acid, enolpyruvic acid, an amino acid, lipoic acid, pantothenic acid, succinic acid, fumaric acid, adipic acid, acetoacetic acid, p-aminobenzoic acid, betahydroxybutyric acid, orotic acid, and creatin, with the proviso that at least one R' is not hydrogen and where at least one R' is acetyl the compound is acyl substituted at $N^4$, or the pharmaceutically acceptable salt thereof.

The objects of the invention are also achieved by administration of acyl derivatives of cytidine comprising compounds having the formula

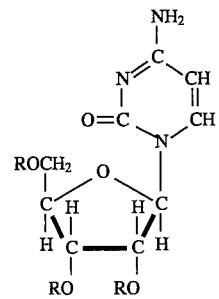
(III)

wherein R is hydrogen or an acyl radical of a metabolite other than $CH_3CHO$—, with the proviso that at least one R is not hydrogen, or the pharmaceutically acceptable salt thereof.

Preferably, the cytidine derivatives are those having formula (III) wherein R is H or an acyl group derived from a carboxylic acid selected from one or more of the group consisting of glycolic acid, pyruvic acid, lactic acid, enolpyruvic acid, an amino acid, a fatty acid other than acetic acid, lipoic acid, pantothenic acid, succinic acid, fumaric acid, adipic acid, acetoacetic acid, p-aminobenzoic acid, betahydroxybutyric acid, orotic acid, and creatin, with the proviso that at least one R is not hydrogen, or the pharmaceutically acceptable salt thereof.

The objects of the invention are also achieved by administering acyl derivatives of cytidine comprising compounds having the formula

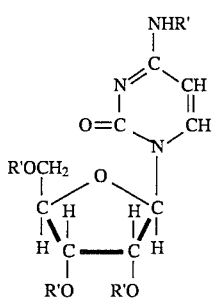

(IV)

wherein R' is hydrogen or an acyl radical of a metabolite other than $CH_3CHO$—, with the proviso that at least one R is not hydrogen, not all R' are derived from a single fatty acid and where $N^4$ alone is substituted, R' is not derived from a fatty acid having 5 or more carbon atoms, or the pharmaceutically acceptable salt thereof.

The preferred cytidine derivatives are those having formula (IV) wherein R' is H or an acyl group derived from a carboxylic acid selected from one or more of the group consisting of glycolic acid, pyruvic acid, lactic acid, enolpyruvic acid, an amino acid, a fatty acid other than acetic acid, lipoic acid, pantothenlc acid, succinic acid, fumaric acid, adipic acid, acetoacetic acid, p-aminobenzoic acid, betahydroxybutyric acid, orotic acid, and creatin, with the provisos that at least one R' is not hydrogen, not all R' are derived from a single fatty acid and where $N^4$ alone is substituted R' is not a fatty acid having 5 or more carbon atoms, or the pharmaceutically acceptable salt thereof.

The invention also includes pharmaceutical compositions which comprise one or more of the novel acylated ribonucleosides described above together with a pharmaceutically acceptable carrier. These compositions may take the form of tablets, dragees, injectable solutions and other forms.

Included among the novel pharmaceutical compositions of the invention are those comprising certain known acyl derivatives of uridine together with a pharmaceutically acceptable carrier. Such compositions include an acyl derivative of uridine having the formula (I) or (II) wherein R and R' are hydrogen or acetyl with the proviso that at least one R or R' is not hydrogen, or a pharmaceutically acceptable salt thereof. The invention also includes pharmaceutical compositions of certain acyl derivatives of cytidine together with pharmaceutically acceptable carriers. Such acyl derivatives include those having the formula (III) or (IV) wherein R and R' are hydrogen or an acyl radical derived from a single fatty acid and wherein not all of said R' are derived from a single fatty acid, or the pharmaceutically acceptable salt thereof.

It has been found that the delivery of exogenous uridine or cytidine to animal tissue may be very substantially enhanced by administering to the animal an effective amount of one or more of the acyl derivatives described above. It has further been found that physiological or pathological conditions of animal tissue may be advantageously treated by supporting the metabolic functions thereof by increasing the bioavailability of uridine or cytidine to that tissue by administering to an animal an effective amount of an acyl derivative as described above.

The invention contemplates the use of these acyl derivatives for a variety of physiological and pathological conditions, including treatment of cardiac insufficiency and myocardial infarction, treatment of liver disease or damage, enhancement of bone healing and muscle performance, treatment of lung disorders, diabetes, central nervous system disorders such as cerebrovascular disorders, Parkinson's disease, senile dementias, demyelinating disorders, and cerebellar ataxia. The compounds of the invention improve the bioavailability of cytidine and uridine by enhancing the transport of these nucleosides across the gastrointestinal tract, the blood-brain barrier, and other biological membranes, and prevent their premature degradation.

Administration of the acyl derivatives of cytidine and uridine offer certain advantages over administration of the underivatized compounds. The acyl substituents can be selected to increase the lipophilicity of the nucleoside, thus improving its transport from the gastrointestinal tract into the bloodstream. The acylated derivatives are effective when administered orally. They are resistant to catabolism by nucleoside deaminases and nucleoside phosphorylases in the intestine, liver, other organs, and the bloodstream. Thus, administration of the acylated derivatives of the invention, either orally or parenterally, allows sustained delivery of high levels of these ribonucleosides to the tissues of an animal.

DESCRIPTION OF THE PREFERRED EMBODIMENTS

Definition of Terms

Figure 2:
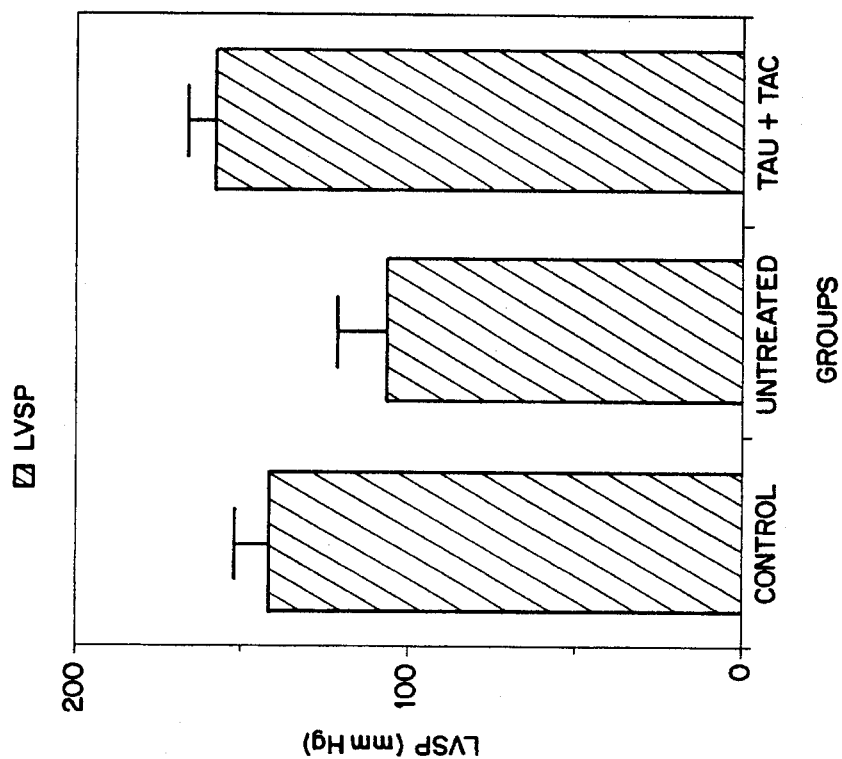
FIG. 2. This figure shows the basal left ventricular systolic pressure of control rats, untreated rats, and rats treated with TAU and TAC after experimental myocardial damage.

A "metabolite" is a chemical compound that is formed by, or participates in, a metabolic reaction. In the context of this application, metabolites include not only acyl substituents known to be synthesized within the human body, but also naturally occurring (but perhaps synthesized rather than extracted) substituents that might be derived from other animal or plant sources. The limiting criteria are that the compound should be substantially nontoxic and biocompatible, and should readily enter into metabolic pathways in vivo, so as to present essentially no toxicity during long-term consumption in the doses proposed. It is preferable that the substituents be metabolized rather than excreted intact (or conjugated through detoxification reactions), as concentration of carboxylic acids within the kidney may lead to undesirable excessive acidity. Therefore, carboxylic acids that normally or easily participate in intermediary, catabolic, or anabolic metabolism are preferred substituents.

"Pharmaceutically acceptable salts" means salts with pharmaceutically acceptable acid addition salts of the nucleoside derivatives of the invention. Such acceptable acids include, but are not limited to, sulfuric, hydrochloric, or phosphoric acids.

"Coadministered" means that each of at least two acyl nucleoside derivatives are administered during a time frame wherein the respective periods of pharmacological activity overlap.

"Acyl derivatives" are derivatives of cytidine or uridine in which a substantially nontoxic organic acyl substituent derived from a carboxylic acid is attached to one or more of the free hydroxyl groups of the ribose moiety of cytidine or uridine with an ester linkage, and/or where such a substituent is attached to a primary or secondary amine in the pyrimidine ring of cytidine or uridine, with an amide linkage. Such acyl substituents include, but are not limited to, those derived from acetic acid, fatty acids, amino acids, lipoic acid, glycolic acid, lactic acid, enolpyruvic acid, pyruvic acid, orotic acid, acetoacetic acid, beta-hydroxybutyric acid, creatinic acid, succinic acid, fumaric acid, adipic acid, and p-aminobenzoic acid. Preferred acyl substituents are compounds which are normally present in the body, either as dietary constituents or as intermediary metabolites, and which are essentially nontoxic when cleaved from the ribonucleoside in vivo.

"Fatty acids" are carboxylic acids having 2–18 carbon atoms. Such fatty acids may be saturated, partially saturated or polyunsaturated.

"Amino acids" include, but are not limited to, glycine, the L forms of alanine, valine, leucine, isoleucine, phenylalanine, tyrosine, proline, hydroxyproline, serine, threonine, cysteine, cystine, methionine, tryptophan, aspartic acid, glutamic acid, arginine, lysine, histidine, ornithine, and hydroxylysine. However, the invention is not so limited, it being within the contemplation of the invention to include other naturally occurring amino acids.

The lipophilic acyl derivatives of uridine and cytidine are useful for enhancing the transport of the nucleotides across the gastrointestinal tract and blood-brain barrier in animals. Foremost among such animals are humans. However, the invention is not intended to be so limiting, it being contemplated that all animals may be treated with the acyl derivatives of the present invention with attendant beneficial effect.

Although the inventors are not bound by a specific mechanism of action, the compounds of the present invention appear to effect their beneficial activity by increasing the bioavailability of cytidine and uridine, and thereby, improving tissue regeneration, repair, performance, resistance to damage, and adaptation to physiological demand. They may work, as well, by increasing the bioavailability of nucleoside anabolites, e.g., nucleotides or nucleotide-derived cofactors. Administration of the nucleosides per se increases their bioavailability but, due to rapid catabolism, this may not result in significant elevation of nucleotide levels; i.e., one doesn't necessarily get an increase in plasma levels because at lower nucleoside levels there is rapid uptake by the cells whereas at higher levels there is saturation and the excess is degraded. The invention is believed to work by delivering a steady supply of nucleoside at low levels.

Preferred acyl derivatives of cytidine or uridine for enhancing transport across biological membranes are those which are more lipophilic than are the parent nucleosides. In general, lipophilic acyl nucleoside derivatives have acyl substituents which are nonpolar (aside from the carboxylate group). Such acyl substituents are derived from acids including, but not limited to, acetic acid, lipoic acid, and fatty acids. One of ordinary skill in the art can determine whether a particular acyl nucleoside derivative is more lipophilic that the underivatized nucleoside using standard techniques, i.e., comparison of the partition coefficients determined in water-octanol mixtures. Following passage of the acylated nucleoside derivative from the gastrointestinal tract into the bloodstream, across the blood-brain barrier, or across other biological membranes, the acyl substituents are cleaved by plasma and tissue esterases (or amidases) to give the free nucleosides.

The rate of removal of the acyl substituents in vivo is a function of the specificity of plasma and tissue deacylating enzymes (primarily esterases or amidases). Thus, fatty acid substituents containing 4 to 8 carbon atoms are cleaved much more rapidly in vivo than are fatty acids with either more or fewer carbon atoms. Acyl substituents attached to an amine group in the pyrimidine ring of cytidine or uridine with an amide linkage are cleaved more slowly than are substituents attached to hydroxyl groups of ribose with an ester linkage.

It is also possible to prepare acyl nucleoside derivatives which contain polar and nonpolar acyl substituents. The polar acyl substituent will retard passage of the nucleoside derivative from the gastrointestinal tract, allowing for a more sustained delivery of the compound into the bloodstream after a single dose. The polar group may be cleaved by esterases, amidases, or peptidases present in the intestinal tract to give a nucleoside with a nonpolar acyl substituent which may then efficiently enter the circulation. Polar acyl substituents may be chosen by one of ordinary skill in the art, without undue experimentation, which are cleaved at a slower rate than are nonpolar acyl substituents.

The acyl derivatives are also less susceptible to degradation of the nucleoside moiety by enzymes in plasma and non-target tissues, and are also less susceptible to elimination from the bloodstream via the kidneys. For parenteral injection, acyl derivatives with polar acyl substituents, which are therefore water soluble yet resistant to premature degradation or elimination, may be used with advantage. Preferred acyl derivatives in such application include glycolate and lactate and those derived from amino acids with polar side chains.

Therapeutic Uses

Administration of the acyl derivatives of cytidine may be useful in treating lung disorders. The acyl derivatives appear to support or enhance phospholipid biosynthesis and surfactant formation in the lung. The alveoli of the lungs are lined with surfactant which reduces the surface tension at the tissue-air interface and enhances inflation of the alveoli during inhalation. The main component of the surfactant, phosphatidyl choline, is derived from cytidine diphosphocholine. Thus, administration of the acylated form of cytidine may support or augment the capacity of pneumocytes to synthesize phospholipids and generate surfactant. This is particularly important in various lung disorders including infant respiratory distress syndrome (IRDS) and in metabolic disorders that affect pulmonary function. The beneficial effects of cytidine acyl derivatives may be enhanced by coadministering uridine acyl derivatives.

In addition, administration of the acyl derivative of cytidine may be useful in treatment of neural disorders. The acyl derivatives may exert their activity by restoring or maintaining brain phospholipid composition during or after a period of cerebral hypoxia or stroke. Administration of the acyl derivative of cytidine may also be useful in slowing the onset or progression of degenerative disorders. Disorders such as senile dementias, cerebrovascular disorders, Parkinson's disease, demyelinating disorders, and cerebral ataxia have been linked to phospholipid levels. The acyl derivatives or uridine may be advantageously coadministered with the acyl derivative of cytidine to enhance its effect.

There are three demyelinating diseases which can be distinguished on the basis of clinical history, examination, and pathological findings. These include multiple sclerosis, acute disseminated encephalomyelitis (including postinfectious and postvaccinal encephalomyelitis) and acute necrotizing hemorrhagic encephalomyelitis. This group of diseases are important neurological disorders both because of the frequency with which they occur and the disability which they cause. Demyelinating diseases share in common the pathological feature of focal or patchy destruction of myelin sheaths in the central nervous system accompanied by an inflammatory response. These diseases may be caused by autoimmunity or viral infections. Only limited regeneration of myelin occurs in multiple sclerosis. See Harrison's *Principles of Internal Medicine,* 10th Edition, Petersdorf et al. (eds.), McGraw-Hill Book Company, New York, N.Y., pp. 2098–2104 (1983).

Thus, administration of cytidine and uridine in the form of these acyl derivatives may act by providing a method of enhancing the regeneration of myelin, thus, ameliorating the symptoms of demyelinating disorders.

Administration of the acyl derivatives of cytidine and uridine may be effective for the treatment of cerebrovascular dementias and Parkinson's disease. Cerebrovascular dementias and Parkinson's disease are part of a group of disorders termed degenerative diseases of the nervous system which cause gradual, generally symmetric, relentlessly progressive wasting away of the neurons. Harrison, supra, p. 2118–2121. Cerebral ataxia is characterized by loss of nerve cells principally affecting the Purkinje cells. In all varieties of cerebellar degeneration, affection of other neuronal systems, such as the cerebral cortex, and basal ganglia or the optic or cochlear neurons may be encountered. See Harrison, ibid., p. 2129–2130.

Therefore, administration of the acyl derivatives of cytidine and uridine may exert their activity enhancing phospholipid biosynthesis and thereby ameliorating the effects of cerebrovascular disorders, Parkinson's disease and cerebral ataxia.

The invention also relates to treatment of physiological or pathophysiological conditions where the body's capacity to synthesize nucleic acids is suboptimal. These conditions include diabetes, senescence, and adrenal insufficiency. Administration of the acyl derivatives of cytidine and uridine may provide a beneficial effect by providing a sustained delivery of high levels of cytidine and uridine to give sufficient pools of nucleotides which are necessary for the biosynthesis of enzymes crucial for cellular self regeneration.

Although the inventors are not bound by any one mode of action, the compositions of the present invention, in and of themselves, appear to act by enhancing nucleotide and nucleic acid synthesis and protein synthesis by providing nucleosides under conditions wherein de novo synthesis is not sufficient for supporting optimal rates of nucleotide and nucleic acid synthesis. Thus, the compounds may find utility in treatment of cardiac insufficiency, myocardial infarction, liver disease including cirrhosis, and by reversing the pathological effects of diabetes by accelerating nucleic acid synthesis and thereby protein synthesis. The compounds of the present invention may also find utility for enhancement of bone healing after fractures.

The acyl derivatives of uridine and cytidine may be administered to improve ventricular function after myocardial infarction or in treating or preventing cardiac insufficiency. Calcium channel blockers or beta adrenergic receptor antagonists may protect the myocardium from influx of exogenous calcium, but they do not improve the capacity of the sarcoplasmic reticulum or mitochondria to take up cytoplasmic calcium ions. The acyl nucleoside derivatives of the invention, which appear to support the cellular mechanisms involved in calcium sequestration, and which thereby preserve or support cellular ATP regeneration, may have significant therapeutic value in preventing or treating some of the deleterious effects of myocardial insults.

The compositions of the present invention may be coadministered with drugs which are used to treat cardiac insufficiency, e.g., digitalis, diuretics and catecholamines.

When the work load of the heart is suddenly increased, as is the case for the surviving portions of the heart after an infarction, the increased load and concurrent sympathetic hyperactivity can result in deficits in myocardial contractibility. When there is a discrepancy between energy supply and demand, severe damage, ultimately related to intracellular calcium overload, can occur. Moreover, successful maintenance of compensatory hyperfunction depends upon increased myocardial RNA synthesis. It is possible to attenuate load-induced myocardial damage, and to promote stable hyperfunction by providing to the heart substances that support the biochemical processes involved in calcium sequestration and RNA biosynthesis.

Uridine and cytidine are useful compounds in this context. Uridine has been reported to be relatively ineffective in supporting myocardial hyperfunction in vivo; however, this may be because uridine is rapidly degraded by plasma and tissue enzymes, which consequently prevents its utilization by the heart. The invention is based partly on the finding that it is possible to improve delivery of uridine to the heart by administering the acyl derivatives which gradually release free uridine into the bloodstream over an extended period of time.

The acyl derivatives of uridine may be administered to treat hypoxia or anoxia. These acyl derivatives appear to act by enhancing biosynthesis of uridine diphosphoglucose, a necessary intermediate in glycogen synthesis, to improve tissue resistance to hypoxia or anoxia and preserve the functional capacity of tissues, in particular cardiac. Uridine acyl derivatives may be used for the treatment of hypoxia, anoxia, ischemia, excessive catecholaminergic stimulation, and digoxin toxicity.

The compounds of the present invention may also find utility in countering some of the long term complications of diabetes, which include neuropathies, arteriopathies, increased susceptibility to both coronary arteriosclerosis and myocardial infarction, and blindness. Since de novo nucleotide synthesis is suppressed in diabetes, exogenous acyl derivatives of nucleosides have therapeutuc value in treating diabetes. In addition, the derivatized forms of the nucleosides may be administered to provide sufficient pools of nucleosides necessary for the biosynthesis of enzymes crucial for cellular self regeneration. Thus, the invention also relates to methods for treating, for example, diabetic liver, aging, or vascular disease by administering the acyl nucleoside derivatives of the invention. The acyl nucleoside derivatives are also useful in supporting or enhancing muscular hypertrophy or hyperfunction in response to increased demand. Such demand may occur after sustained muscular exertion. The acyl derivatives may also be administered after sustained nonuse, such as after removal of a cast following the healing of a bone fracture.

Preferred acyl substituents include acetyl, palmitoyl, and valeroyl groups. Preferred acyl nucleoside derivatives include 2',3',5'-triacetyl cytidine, 2',3',5'-triacetyl uridine, 2',3',b 5'-tripalmitoyl uridine, 2',3',5'-tripalmitoyl cytidine, 2',3',5'-tripalmitoyl uridine, 2',3',5'-trivaleroyl cytidine and 2',3',5'-trivaleroyl uridine. It can be advantageous to coadminister acyl derivatives of both cytidine and uridine.

Typical dosage forms are equivalent to 10 to 3000 mg of cytidine and/or uridine in the form of their acyl derivatives or the pharmaceutically acceptable salt thereof, 1 to 3 times per day. This corresponds to, for example, 15 to 4500 mg of 2',3',5'-triacetyl cytidine and 2',3',5'-triacetyl uridine For treatment of cardiac insufficiency, myocardial infarction and the consequences of hypertension, a composition comprising 25 to 100 mole percent of the acyl derivative of uridine may be coadmnistered together with 75 to 0 mole percent of the acyl derivative of cytidine with the proviso that the amounts of the acyl derivatives of cytidine and uridine do not exceed 100 mole percent. For example, 1125–4500 mg of 2',3',5'-triacetyluridine may be administered with 0–3475 mg of 2',3',5'-triacetylcytidine For treatment of cerebrovascular disorders, senile dementias, bone breakage, diabetes, liver damage and disease, and senescence, and to increase muscle performance, a composition comprising 25 to 75 mole percent of the acyl derivative of uridine may be coadministered together with 75 to 25 mole percent of the acyl derivative of cytidine with the proviso that the amount of the acyl derivatives of uridine and cytidine do not exceed 100 mole percent. For example, 1125–3375 mg of 2',3',5'-triacetyluridine may be coadministered with 1125–3375 mg of 2',3',5'-triacetyl cytidine.

For treatment of respiratory distress syndrome, 25 to 100 mole percent of the acyl derivative of cytidine may be coadministered with 75 to 0 mole percent of the acyl derivative of uridine with the proviso that the amounts of the acyl derivatives of uridine and cytidine do not exceed 100 mole percent. For example, 1125–4500 mg of 2',3',5'-triacetyl cytidine may be coadministered together with 0–3375 mg of 2',3',5'-triacetyl uridine.

Examples of Therapeutic Administration

Cardiac Insufficiency

Acyl derivatives of cytidine and uridine are useful in the treatment of several varieties of cardiac insufficiency. They are effective in supporting sustained compensatory hyperfunction in the case of increased load upon the heart in hypertension, for example, or especially in supporting the function of the surviving portions of the heart after a myocardial infarction. In this latter situation, a mixture of acyl derivatives of cytidine and uridine may be given as soon after the onset of the infarction as possible, followed by chronic oral administration of a suitable formulation of acyl derivatives of these nucleosides in doses of approximately 0.5 to 3.0 grams per day of each. These compounds may be used advantageously in conjunction with conventional treatments of myocardial infarction. The nucleoside derivatives have the unique advantage of protecting the heart against damage secondary to overload, hypoxia, or catecholamines without reducing the functional capacity of the heart, since they act by enhancing the metabolic integrity of the myocardium, in particular by improving calcium handling. The nucleoside derivatives may also be administered prophylactically to patients at risk for myocardial infarction or cardiac insufficiency.

For treatment of chronic cardiac insufficiency, which leads to congestive heart failure, acyl derivatives of cytidine and uridine may be administered orally in doses ranging from 0.5 to 3 grams per day of each nucleoside. The nucleosides may be used in conjunction with other agents such as digitalis derivatives or diuretics. In addition to improving myocardial function directly, the nucleoside derivatives reduce digitalis toxicity without impairing its clinical efficacy.

Diabetes

In many tissues of diabetic subjects, cellular pyrimidine nucleotide levels are reduced; this may contribute to some of the long-term complications of diabetes, including arteriopathies, neuropathies, and decreased resistance of the myocardium to mechanical or biochemical stress. These complications are related to malfunctions in tissue calcium handling, in which pyrimidine nucleotides play key roles. It has been reported that daily intramuscular injection of cytidine and uridine reverses the depression in peripheral nerve conduction velocity in diabetic humans (C. Serra, Rif. Med. 85:1544 [1971]). It is preferable to administer acyl derivatives of cytidine and uridine orally in suitable formulations. Doses equivalent to 0.5 to 3 grams of cytidine and uridine are administered daily, in conjunction with conventional anti-diabetic treatments. The nucleoside derivatives are particularly useful in non-insulin dependent diabetes.

Neurological Disorders

In the treatment of the consequences of cerebrovascular disorders, e.g., stroke and chronic or acute cerebrovascular insufficiency, acyl derivatives of cytidine and uridine, particularly those formulated to pass through the blood-brain barrier after oral administration, may be administered in oral doses ranging from 0.5 to 3.0 grams of each nucleoside per day for at least several months.

In Parkinson's disease, acyl cytidine derivatives are particularly useful, and may be given in conjunction with the conventional treatment of choice, L-DOPA. The cytidine derivatives, administered in oral doses of 0.5 to 3.0 grams per day, may permit satisfactory clinical maintenance on reduced dosages of L-DOPA, which is advantageous because L-DOPA has undesirable side effects.

Methods of Preparation of the Compounds

The acyl derivatives of the invention may be prepared by the following general methods. When the acyl substituent has groups which interfere with the acylation reactions, e.g., hydroxyl or amino groups, these groups may be blocked with protecting groups, e.g., t-butyldimethylsilyl esters or t-BOC groups, respectively, before preparation of the anhydride. For example, lactic acid may be converted to 2-(t-butyldimethylsiloxy)propionic acid with t-butyldimethylchlorosilane, followed by hydrolysis of the resulting silyl ester with aqueous base. The anhydride may be formed by reacting the protected acid with DCC.

In the case of amino acids, the N-t-BOC derivative may be prepared, using standard techniques, which is then converted to the anhydride with DCC.

Derivatives containing acyl substituents with more than one carboxylate group (e.g., succinate, fumarate, or adipate) are prepared by reacting the acid anhydride of the desired dicarboxylic acid with a 2'-deoxyribonucleoside in pyridine.

For example, the $O^{2'},O^{3'},O^{5'}$-triacyl derivatives of uridine may be prepared by a modified procedure disclosed by Nishizawa et al., *Biochem. Pharmacol.* 14:1605 (1965). To one equivalent of uridine in pyridine is added 3.1 equivalents of an acid anhydride (acetic anhydride, butyric anhydride, etc.), and the mixture heated to 80°–85° C. The triacyl derivative may then be isolated using standard techniques. Alternatively, uridine may be treated with 3.1 equivalents of a desired acid chloride (acetyl chloride, palmitoyl chloride, etc.) in pyridine at room temperature (See Example IV).

The 5'acyl derivative of uridine may be prepared according to Nishizawa et al. by reacting uridine with 1 equivalent of the acid anhydride of the desired acyl compound in pyridine at room temperature. The reaction is then heated to 80°–85° C. for two hours, cooled, and the 5'-acyl derivative isolated by standard techniques and purified by chromatography. Alternatively, the 5'-acyl derivative of uridine may be prepared by treating uridine, in pyridine and DMF at 0° C., with 1 equivalent of the acid chloride derived from the desired acyl compound. The 5'-acyl derivative of uridine may then be isolated by standard techniques and purified by chromatography (see Example V).

The 2',3'-diacyl derivatives of uridine may be prepared by a procedure adapted from Baker et al., *J. Med. Chem.* 22: 273 (1979). The 5'-hydroxyl group is selectively protected with 1.2 equivalents of t-butyldimethylsilyl chloride in DMF containing imidazole, at room temperature. The 5'-t-butyldimethylsilyl derivative of uridine is isolated by standard techniques, then treated with 2.1 equivalents of the acid anhydride of the desired acyl compound in pyridine at 0°–5° C. The resulting 5'-t-butyl dimethylsiloxy-2',3'-diacyl uridine is then treated with tetrabutylammonium fluoride and the 2',3'-diacyl derivative of uridine is isolated by standard techniques (see Example VI).

The secondary amine of 2',3',5'-triacyl uridine may then be acylated according to Fujii et al., U.S. Pat. No. 4,425,335, which involves treatment with 1.1 equivalents of an acid chloride in an aprotic solvent containing 1–5 equivalents of an organic base, e.g., aromatic amines such as pyridine, trialkylamines, or N,N-dialkylanilines. Using this procedure, a tetraacyl derivative of uridine may be prepared which has an acyl substituent on the amino group which is different from the acyl substituents at the 2',3' and 5' hydroxy groups (see Example VII).

The 2',3',5'-triacyl derivatives of cytidine may be prepared according to a method adapted from Gish et al., *J. Med. Chem.* 14:1159 (1971). For example, cytidine hydrochloride may be treated with 3.1 equivalents of the desired acid chloride in DMF The 2',3',5'-triacyl derivative may then be isolated using standard techniques (see Example VIII).

The 5'-acyl derivative of cytidine may be prepared according to Gish et al., supr.a, by treatment of cytidine hydrochloride with 1.1 equivalents of an acid chloride in DMF, followed by isolation of 5'-acyl cytidine by standard techniques (see Example IX).

Selective acylation of the $N^4$-amine of cytidine accomplished according to the procedure disclosed by Sasaki et al., *Chem. Pharm. Bull.* 15:894 (1967). This involves treatment of cytidine with 1.5 equivalents of an acid anhydride in pyridine and DMF. The $N^4$-acyl derivative of cytidine may then be isolated by standard techniques (see Example X).

Alternatively, the $N^4$-acyl derivative of cytidine may be prepared by treatment of cytidine with an acyl anhydride in pyridine or a mixture of pyridine and DMF. Another procedure for the selective preparation of $N^4$-acyl cytidine involves selective acylation with an acid anhydride in a water-water miscible solvent system according to Akiyama et al., *Chem. Pharm. Bull.* 26:981 (1978) (see Example X).

Tetraacyl cytidine derivatives, where all the acyl groups are the same, may be prepared by treating cytidine with at least 4 molar equivalents of an acid anhydride in pyridine at room temperature. The tetraacyl cytidine may then be isolated using standard techniques (see Example XI).

To prepare compounds in which the acyl substituent on the $N^4$ amino group is different from the acyl substituents on the hydroxyl groups of the ribose ring (e.g., $N^4$-palmitoyl 2',3',5'-triacetyl cytidine), the desired acyl substituent is selectively attached to the $N^4$ amino group as described above, and then the hydroxyl groups are acylated with their intended substituents. Alternatively, the substituents on the ribose moiety may be attached prior to attachment of the substituent of the $N^4$ amino group, again using methods described above.

The invention also relates to the use of 2',3',5'-tri-O-nicotinoyl cytidine to treat the above-mentioned conditions 2',3',5'-tri-O-nicotinoyl cytidine may be prepared according to the procedure dis closed in German Patent No. 2,347,226.

The invention further relates to the use of $N^4$, $O^{2'}$, $O^{3'}$, $O^{5'}$-triacyl cytidine and the $O^{2'},O^{3'},O^{5'}$-triacetyl uridine to treat the above-mentioned condition where the acyl group contains 3–18 carbon atoms. Tetraacyl cytidines may be prepared, for example, by the method disclosed by Honjo, M., et al., Great Britain Patent No. 1,297,398 (1970).

Compositions within the scope of this invention include all compositions wherein each of the components thereof is contained in an amount effective to achieve its intended purpose. Thus, the compositions of the invention may contain one or more acyl nucleoside derivatives of uridine or cytidine in amounts sufficient to result, upon administration, in increased plasma or tissue levels of cytidine or uridine and the acyl derivatives thereof, which thereby produce their desired effect.

In addition to the pharmacologically active compounds, the new pharmaceutical preparations may contain suitable pharmaceutically acceptable carriers comprising excipients and auxiliaries which facilitate processing of the active compounds into the preparations which may be used pharmaceutically. Preferably, the preparations, particularly those preparations which can be administered orally and which can be used for the preferred type of administration, such as tablets, dragees, and capsules and also preparations which can be administered rectally, such as suppositories, as well as suitable solutions for administration by injection or orally, contain about from 0.1 to 99%, preferably from about 10–90%, of the active compound(s), together with the excipient.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compound(s) with solid excipients, optionally grinding a resulting mixture and processing the mixture of granules, after adding suitable auxiliaries, if desired or necessary, to obtain tablets or dragee cores.

Suitable excipients are, in particular, fillers such as sugars, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethyl cellulose, sodium carboxymethyl cellulose, and/or polyvinyl pyrrolidone. If desired, disintegrating agents may be added such as the above-mentioned starches and also carboxymethyl-starch, cross-linked polyvinyl pyrrolidone, agar, or algenic acid or a salt thereof, such as sodium alginate. Auxiliaries are, above all, flow-regulating agents and lubricants, for example, silica, talc, stearic acid or salts thereof, such as magnesium stearate or calcium sterate, and/or polyethylene glycol. Dragee cores are provided with suitable coatings which, if desired, are resistant to gastric juices. For this purpose, concentrated sugar solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxylpropylmethylcellulose phthalate are used. Dye stuffs or pigments may be added to the tablets or dragee coatings, for example, for identification or in order to characterize different combinations of compound doses. Other pharmaceutical preparations which can be used orally include push-fit capsules made of gelatin, as well as soft-sealed capsules made of gelatin and a plasticizer such as glycerol or sorbitol. The push-fit capsules contain the active compound(s) in the form of granules which may be mixed with fillers such as lactose, binders such as starches and/or lubricants such as talc or magnesium sterate, and, optionally, stabilizers. In soft capsules, the active compounds are preferably dissolved or suspended in suitable liquids such as fatty oils, liquid paraffin, or polyethylene glycols. In addition, stabilizers may be added.

Possible pharmaceutical preparations which can be used rectally include, for example suppositories which consist of a combination of active compounds with a suppository base. Suitable suppository bases are, for example, natural or synthetic triglycerides, paraffin hydrocarbons, polyethylene glycols or higher alkanols. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water soluble form, for example, water soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may include substances which increase the viscosity of the suspension which include, for example, sodium carboxymethylcellulose, sorbitol, and/or dextran. Optionally, the suspension may also contain stablizers.

The following examples are illustrative, but not limiting, of the methods and compositions of the present invention. Other suitable modifications and adaptations of the variety of conditions and parameters normally encountered in clinical therapy and which are obvious to those skilled in the art and are within the spirit and scope of this invention.

EXAMPLES

Example I: Comparison of the Bioavailability of Uridine and Acyl Uridine Derivatives in Rats Silastic catheters were implanted into the right jugular veins of anesthetized male F344 rats (Retired Breeders, 450–500 grams). After three days of recovery from surgery, the animals were placed in deep cylindrical cages, and their catheters were extended with a lengthened polyvinyl tubing, so that blood samples would be withdrawn without disturbing the rats. Basal blood samples were taken and the animals were divided into four groups, each containing four rats. Each group received a different one of each of the following compounds; uridine, 2',3',5'-tri-O-acetyl uridine, cytidine, or 2',3',5'-tri-O-acetyl cytidine The compounds were given in equimolar dosages (0.28 moles/kg) by intubation into the stomach. At intervals of 0.5, 1, 2, 3, and 4 hours after administration, blood samples (0.3 ml) were withdrawn and processed for subsequent assay of cytidine or uridine content by HPLC. In the rat, plasma levels of uridine were significantly higher for at least four hours following ingestion of tri-O-acetyl uridine than after ingestion of an equimolar dose of uridine.

Example II: Comparison of the Bioavaiability of Uridine and Acyl Uridine Derivatives in Humans After an overnight fast, a basal venous blood sample was withdrawn from a human subject and then 0.76 mmoles/kg (28 mg/kg—2 grams in a 70 kg subject) of tri-O-acetyl uridine was ingested along with 100 ml of water. Blood samples (0.5 ml) were withdrawn at intervals of 1, 2, 3, and 4 hours after ingestion of the compound and were processed for subsequent determination of plasma uridine content by HPLC. On a separate day, the same procedure was carried out, except that an equal molar dose (18 mg/kg—1.3 grams in a 70 kilogram subject) of uridine was ingested instead of the acyl derivative. The plasma level of uridine was substantially higher following ingestion of tri-O-acetyl uridine than after ingestion of the equal molar dose of uridine. Uridine levels were sustained in the useful therapeutic range (than 10 micromolar) for at least four hours after oral administration of tri-O-acetyl uridine. After administration of oral uridine, plasma levels of the nucleoside exceeded 10 micromolar at only one point in time (two hours).

Example III: Restoration of Depressed Myocardial Function with Acylated Pyrimidine Ribonucleosides The experiment described within this example was designed to determine whether providing exogenous tri-acetyl uridine and triacetyl cytidine could help to restore pump function in the ventricular myocardium after experimental depression of ventricular function.

Figure 5:
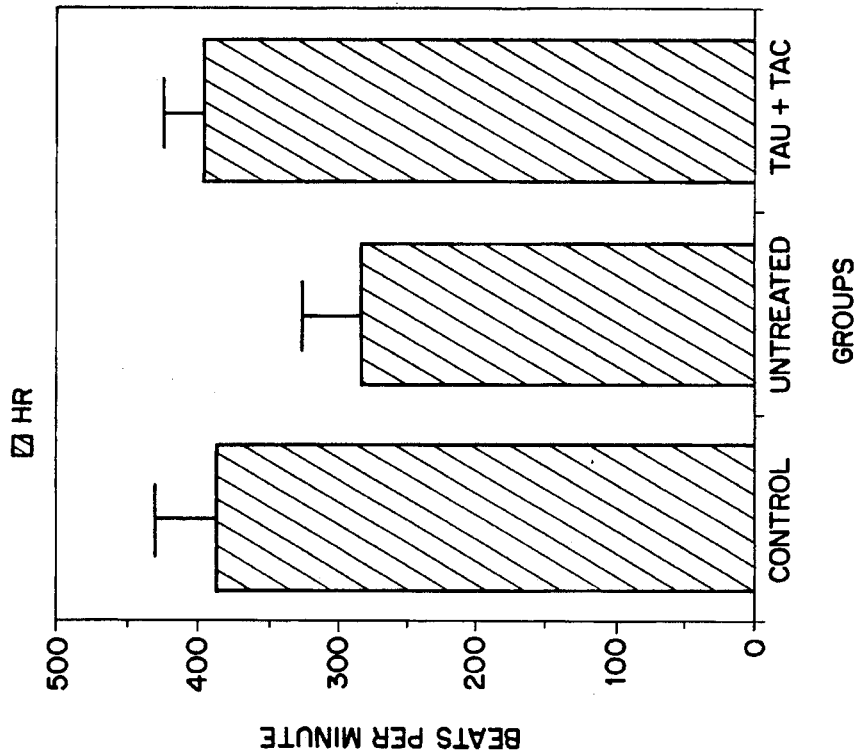
FIG. 5. This figure shows the basal heart rate of control rats, untreated rats, and rats treated with TAU and TAC after experimental myocardial damage.
Figure 8:
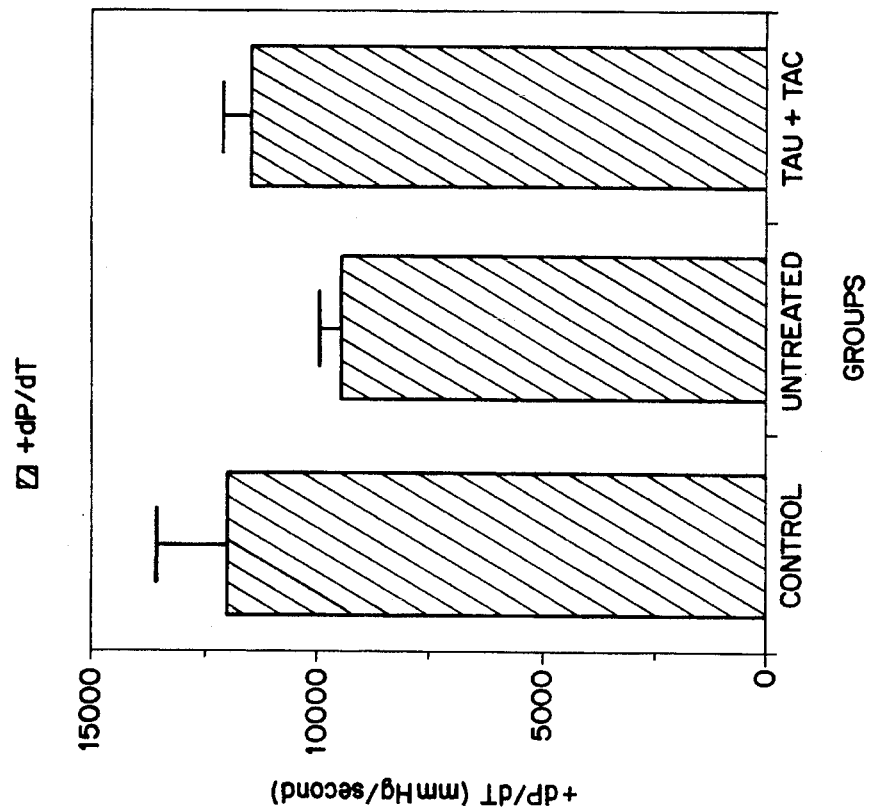
FIG. 8. This figure shows the maximum rate of ventricular contraction (maximum) of control rats, untreated rats, and rats treated with TAU and TAC and norepinephrine after experimental myocardial damage.
Figure 7:
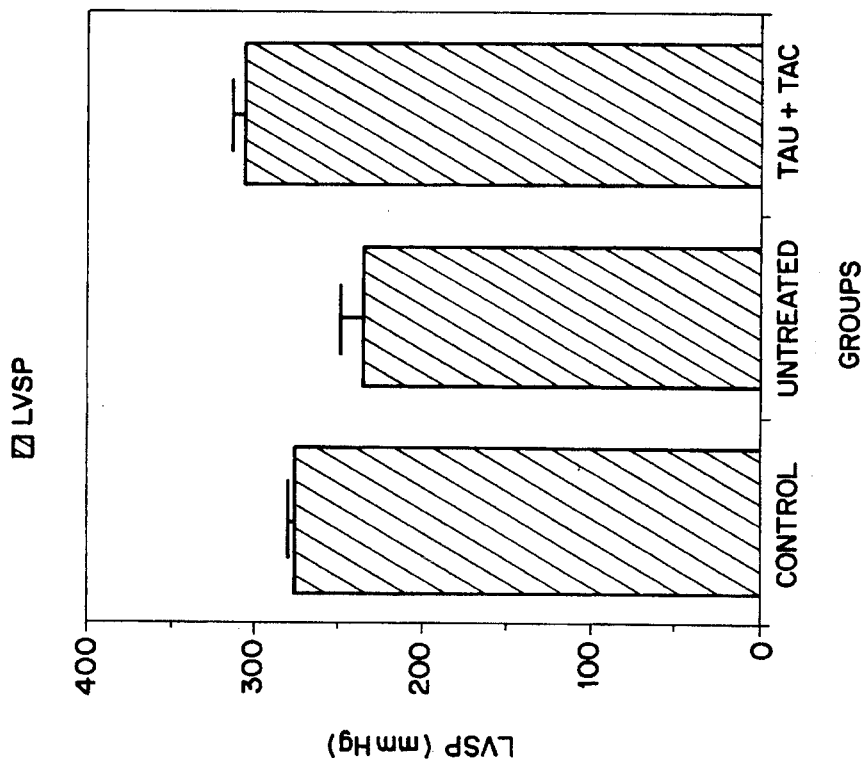
FIG. 7. This figure shows the maximum left ventricular systolic pressure of control rats, untreated rats, and rats treated with TAU and TAC and norepinephrine after experimental myocardial damage.
Figure 10:
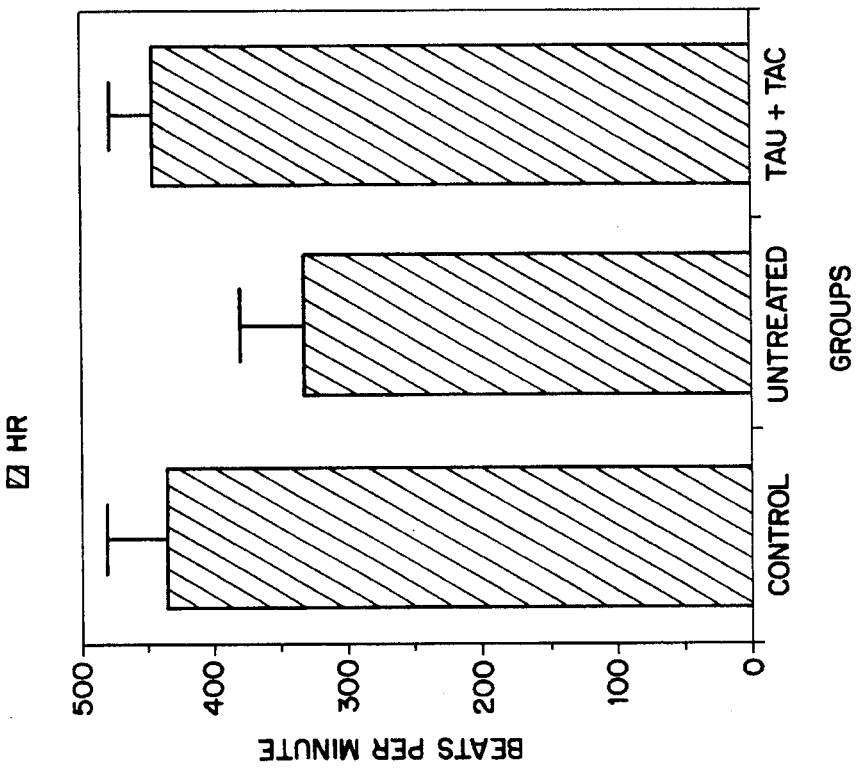
FIG. 10. This figure shows the heart rate (maximum) of control rats, untreated rats, and rats treated with TAU and TAC and norepinephine after experimental myocardial damage.
Figure 9:
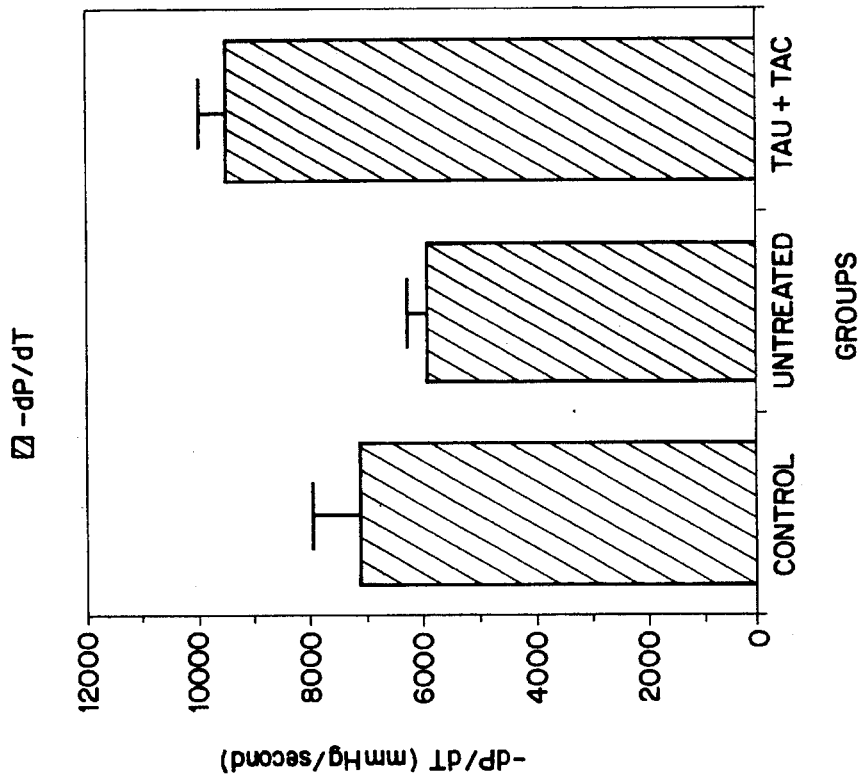
FIG. 9. This figure shows the maximum rate of ventricular relaxation (maximum) of control rats, untreated rats, and rats treated with TAU and TAC and norepinephrine after experimental myocardial damage.

Experimental myocardial damage was induced in anesthetized (Nembutal, 50 mg/kg i.p.) male F344 rats (250 grams) by constricting the abdominal aorta to an internal diameter of 0.67 mm, followed by injection of a single dose of isoproterenol hydrochloride (5 mg/kg s.c.). A mixture of these parameters were significantly restored toward normal, compared to animals treated only with isoproterenol (FIGS. 1–4). Heart rate was also depressed after experimental myocardial damage (FIG. 5).

TABLE 1

| TREATMENT | Basal Heart Performance | | | | |
| --- | --- | --- | --- | --- | --- |
| | LVSP (mmHg) | HR (bpm) | +dP/dT (mmHg/sec) | −dP/dT (mmHg/sec) | HR × LVSP (mmHg/min) |
| Control | 141 ± 11 | 386 ± 46 | 6000 ± 348 | 5640 ± 528 | 55,766 ± 10,407 |
| AC + Saline | 107 ± 14* | 283 ± 44 | 4080 ± 600* | 3120 ± 840* | 32,633 ± 9,115* |
| AC + TAU & TAC | 158 ± 9 | 398 ± 28 | 6000 ± 480 | 5640 ± 300 | 63,518 ± 6,624 |

* = Significantly different from control value (P .02)
Abbreviations:
AC = Aorta constriction + isoproterenol
TAU = Triacetyl uridine
TAC = Triacetyl cytidine
LVSP = Left ventricular systolic pressure
HR = Heart rate
+dP/dT = Maximum rate of ventricular contraction
−dP/dT = Maximum rate of ventricular relaxation

TABLE 2

| TREATMENT | Maximal Heart Performance | | | | |
| --- | --- | --- | --- | --- | --- |
| | LVSP (mmHg) | HR (bpm) | +dP/dT (mmHg/sec) | −dP/dT (mmHg/sec) | HR × LVSP (mmHg/min) |
| Control | 277 ± 3 | 436 ± 46 | 12000 ± 1580 | 7200 ± 408 | 120,833 ± 13,147 |
| AC + Saline | 238 ± 12* | 334 ± 47 | 9480 ± 480* | 6000 ± 360* | 80,860 ± 15,271* |
| AC + TAU & TAC | 308 ± 9 | 446 ± 33 | 11520 ± 600 | 9600 ± 480 | 138,056 ± 12,234 |

Figure 1:
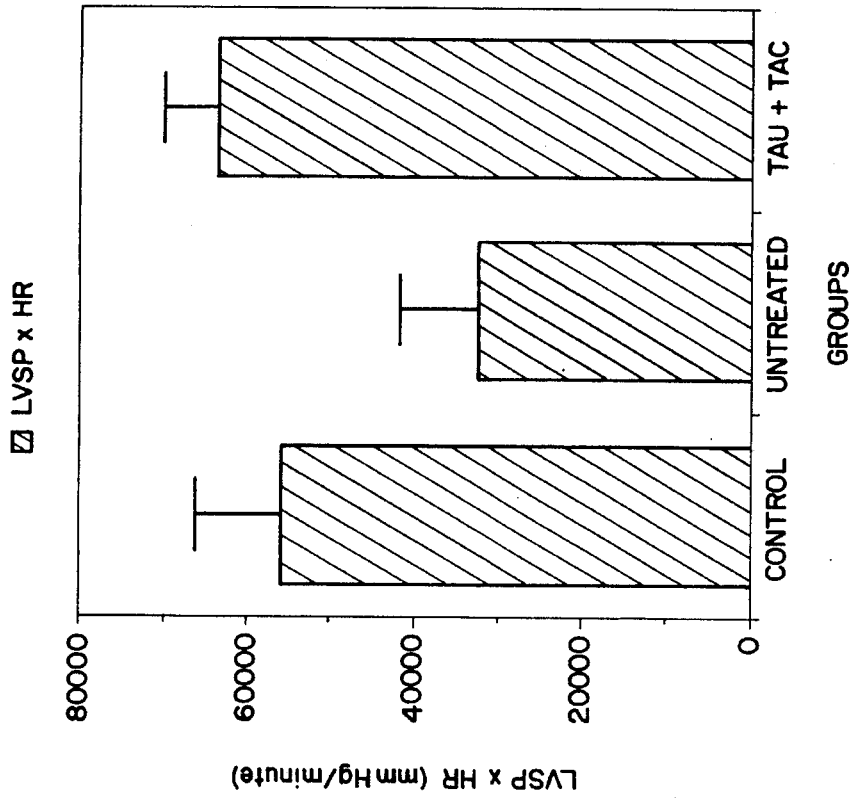
FIG. 1. This figure shows the basal heart work output for undamaged (received only saline) rats, rats with experimental myocardial damage but untreated (received only saline) and rats treated with triacetyluridine (TAU) and triacetylcytidine (TAC) after experimental myocardial damage.
Figure 3:
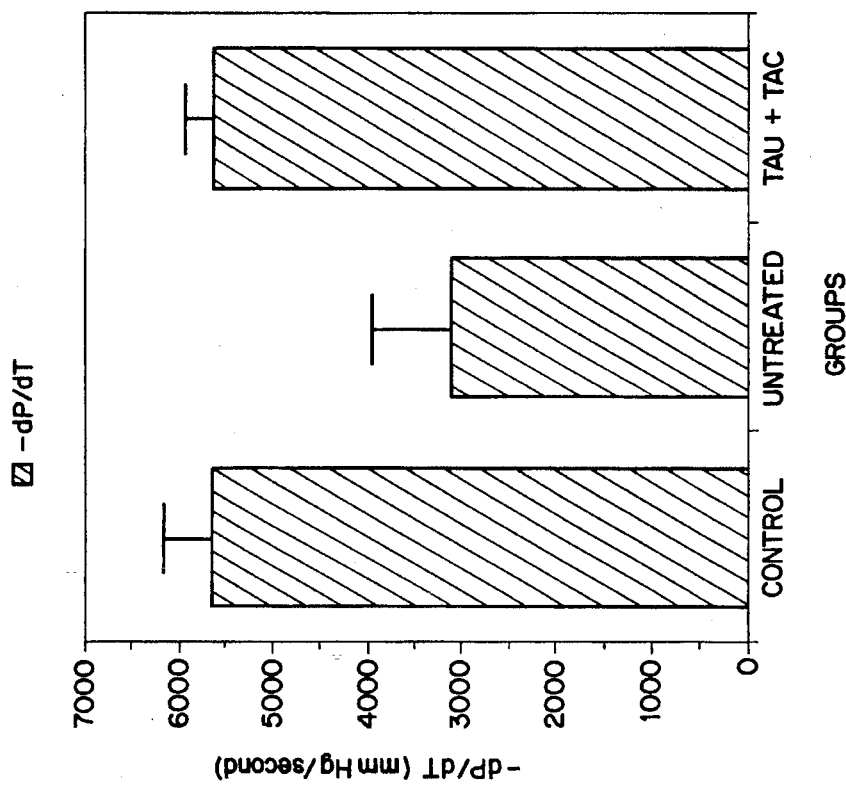
FIG. 3. This figure shows the basal maximum rate of ventricular contraction of control rats, untreated rats, and rats treated with TAU and TAC after experimental myocardial damage.
Figure 4:
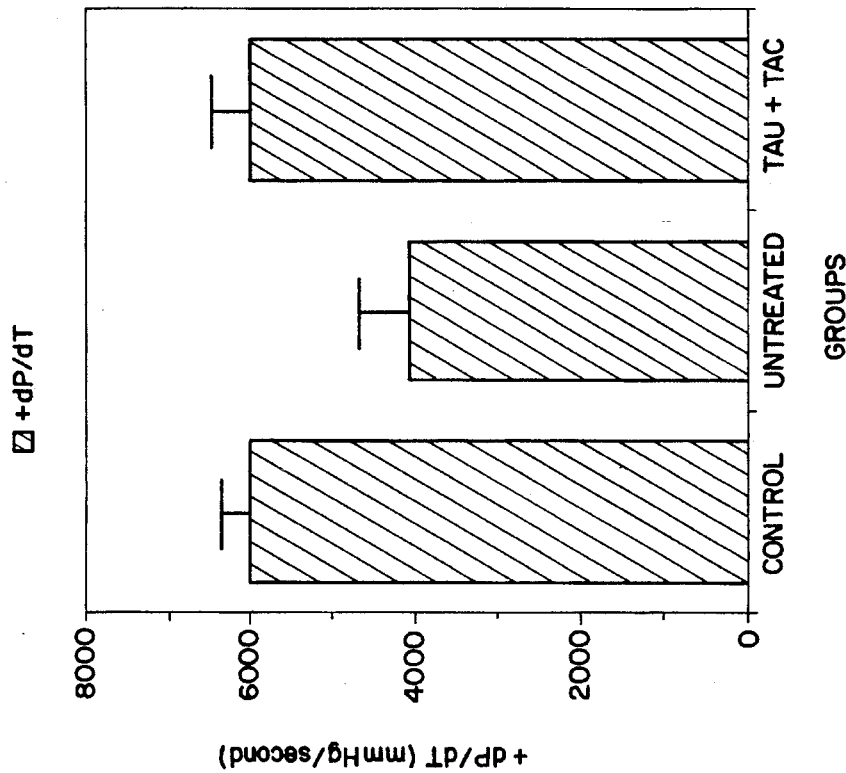
FIG. 4. This figure shows the basal maximum rate of ventricular relaxation of control rats, untreated rats, and rats treated with TAU and TAC after experimental myocardial damage.
Figure 6:
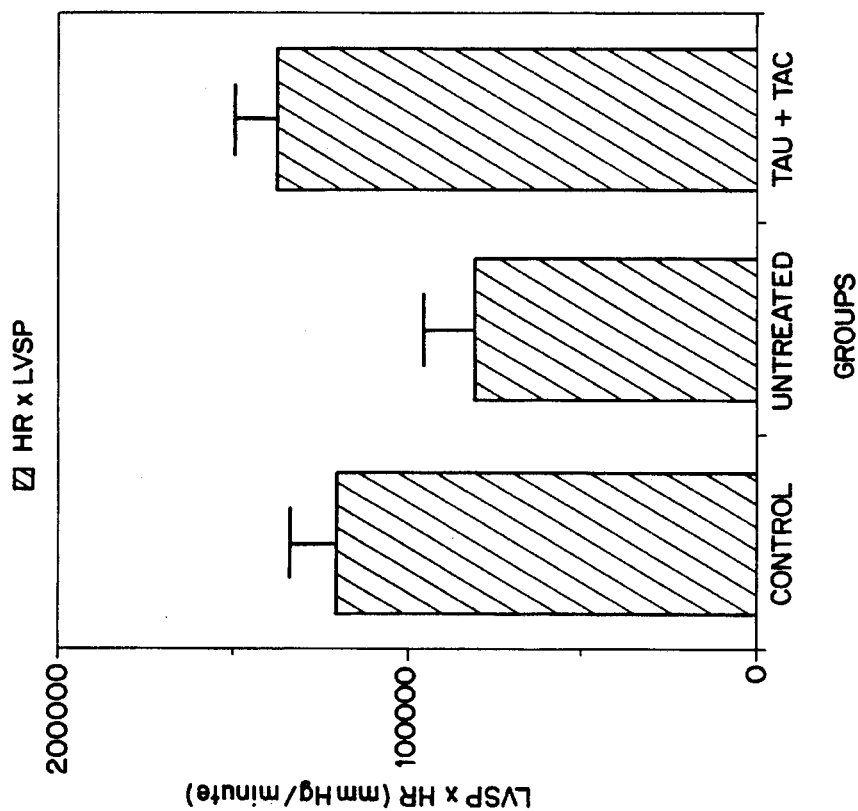
FIG. 6. This figure shows the maximum heart work output of control rats, untreated rats, and rats treated with TAU and TAC and norepinephrine after experimental myocardial damage.

* = Significantly different from control value (P .02)
(Abbreviations are the same as in FIG. 1.)

triacetyl cytidine and triacetyl uridine (590 mg/kg of each) was administered immediately after, and again 1 hour and 20 hours after aorta constriction and administration of isoproterenol. Some animals received injections of saline instead of the acetylated nucleosides (untreated), and a group of animals also received saline injections but were not subjected to aorta constriction or treatment with isoproterenol (controls). Ventricular function was determined 24 hours after aortic constriction. Animals were anesthetized with sodium pentobarbital (50 mg/kg i.p.), and a catheter was implanted in the right jugular vein for administration of norepinephrine. A second catheter (Intramedic PE-50) was inserted into the left ventricle of the heart via the right carotid artery. Left ventricular systolic pressure (LVSP), the maximum rate of ventricular contraction and relaxation (+dP/dT and −Dp/dT, respectively) and heart rate (HR) were measured directly via this catheter, using a Statham-type pressure transducer interfaced to a Stoelting Physioscribe II polygraph. Values of these parameters were recorded, before and after i.v. administration of 9.1 ml of norepinephrine bitartrate at concentrations of $10^{-6}, 10^{-5}$, and $10^{-4}$M. Electrocardiograms were also recorded with this apparatus, using stainless steel needle electrodes inserted subcutaneously in the forelimbs. Heart work output was calculated as the product of ventricular systolic pressure and heart rate.

Aorta constriction in conjunction with isoproterenol administration resulted in substantial decrements in myocardial performance compared to intact controls. Left ventricular systolic pressure, +dP/dT, −dP/dT, and heart work output were all significantly depressed (Table 1; FIGS. 1–4). In the animals that received acetylated pyrimidines after aorta constriction and administration of isoproterenol, all of these parameters were significantly restored toward normal, compared to animals treated only with isoproterenol (FIGS. 1–4). Heart rate was also depressed after experimental myocardial damage (FIG. 5).

The parameters of myocardial performance were monitored in the same rats following administration of 0.1 ml of $10^{-4}$M norepinephrine bitartrate. These values represent the maximal performance of the heart, and are displayed in Table 2 and FIGS. 6–10.

Discussion

Providing exogenous nucleosides to the myocardium by administering the acyl nucleoside derivatives of the invention prevents or alleviates the impairments in myocardial performance that normally accompany cardiac hyperfunction and hypertrophy that follows a sustained increase in load upon the heart. Such an increase in workload occurs in the surviving portions of the heart following a severe myocardial infarction. Therefore, pyrimidine nucleosides or acylated derivatives are useful therapeutic agents in the treatment of or prevention of heart failure following myocardial infarction. There are currently no therapeutic agents in contemporary clinical practice that operate by supporting the biochemical mechanism underlying myocardial energy metabolism or capacity for adaptation to sustained increases in workload. These results indicate that such an approach yields significant functional benefits.

Example IV: Preparation of 2',3',5'-Triacyl Uridine From Acid Anhydrides

To 1 gram of uridine dissolved in 20 ml anhydrous pyridine (previously dried over potassium hydroxide) is added at room temperature 3.1 molar equivalents of the acid anhydride of the desired acyl compound (e.g., acetic anhydride, lactate anhydride, butyric anhydride, etc.). The reaction mixture is then heated to 80°–85° C. for 2 hours, cooled, poured into ice water, and the esters recovered by extraction three times with equal volumes of chloroform. The chloroform is then washed with ice-cold 0.01N sulfuric acid, 1% aqueous sodium bicarbonate, and finally water. After drying with sodium sulfate, the chloroform is evaporated and the residual oil or crystals are subjected to chromatography (adapted from Hishizawa et al., *Biochem. Pharmacol.* 14:1605 (1965)).

From acid chlorides:

To 1 gram of uridine in 20 ml anhydrous pyridine is added, at 5° C., 3.1 molar equivalents of the acid chloride of the desired acyl compound (e.g., palmitoyl chloride, acetyl chloride, etc.). The mixture is held at room temperature overnight, added to ice water, and worked up as indicated above (adapted from Nishizawa et al., *Biochem. Pharmacol.* 14:1604 (1965)).

Example V: Preparation of 5-Acyl Uridine

To 1 gram of uridine dissolved in 20 ml anhydrous pyridine is added, at room temperature, 1.0 molar equivalent of the acid anhydride of the desired acyl compound. The reaction is then heated to 80°–85° C. for two hours, cooled, poured into ice water, and the esters recovered by extraction three times with equal volumes of chloroform. The chloroform is then washed ice cold 0.01N sulfuric acid, 1% aqueous sodium bicarbonate, and finally water. After drying with sodium sulfate, the chloroform is evaporated and the residual oil or crystals are subjected to chromatography. The major product, which is isolated by chromatography, is the 5'-substituted ester (adapted from Nishizawa et al., *Biochem. Pharmacol.* 14:1605 (1965)).

Alternatively, selective 5'-acylation of uridine may be accomplished by suspending 1 gram of uridine in 30 ml of 1:1 pyridine:N,N-dimethylformamide cooled to 0° C. in an ice bath. 1.0 molar equivalent of the acid chloride of the desired acyl compound is added dropwise to the mixture, which is stirred at 0° C. for 12–24 hours. 3 ml of water is added, and then the solvents are evaporated in vacuo at 50° C. The residue is dissolved in methanol and adsorbed onto approximately 3 grams of silica gel, and the excess solvent is evaporated off. Toluene is evaporated three times from the solid mass, and the whole is loaded onto a 3×15 cm slurry-packed column of silica gel in chloroform, and eluted with a linear gradient of chloroform (200 ml) to 20:80 methanol:chloroform (200 ml). The appropriate fractions, as determined by TLC, are combined, and the solvents are evaporated to yield the desired product that is either recrystallized or dried in vacuo to a glass (adapted from Baker et al., *J. Med. Chem.* 21:1218 (1978)).

Example VI: Preparation of 2',3'-Diacyl Uridine

To a stirred suspension of 1 gram of uridine in 20 ml dry N, N-dimethylformamide is added 2.4 molar equivalents of imidazole followed by 1.2 molar equivalents of t-butyldimethylchlorosilane. The mixture is stirred with protection from moisture at room temperature for 20 hours, at which time the solvent is removed at 50° C. in vacuo. The residue is dissolved in 15 ml of ethyl acetate, the solution is washed with 10 ml of water, and the extract is dried with magnesium sulfate and evaporated to give a syrup. Crystallization from 10 ml of hot chloroform, to which is added hexane to the point of opalescence, followed by slow cooling to room temperature, gives 5'-(t-butyldimethylsilyl) uridine.

To a stirred suspension of 1 gram of 5'-(t-butyldimethylsilyl) uridine in 15 ml of dry pyridine cooled to 0° C. is added 2 1 molar equivalents of the appropriate acid anhydride of the desired acyl compound, and the mixture is stirred with protection from moisture for 20 hours at 0°–5° C., at which time the reaction is terminated by addition of a few ml of water. The solvent is evaporated and the residue is dissolved in 15 ml of chloroform, washed with 2×15 ml of saturated sodium hydrogen carbonate, and then with water, dried (magnesium sulfate) and evaporated to give a thick, clear syrup, which is then dried in vacuo at 25° C.

To a stirred solution of the above acylated product in 30 ml of dry tetrahydrofuran is added 0.2 ml glacial acetic acid, followed by 1.5–2.3 grams of tetrabutylammonium fluoride, and the reaction is monitored by TLC (9:1 chloroform methanol). Upon complete removal of the t-butyldimethylsilyl group from the 5' hydroxyl group of the acylated uridine derivative, the fluoride is removed from the mixture by filtration through a layer of 30 grams of silica gel, and the products are eluted with tetrahydrofuran. The crude product, obtained upon evaporation of the solvent is recrystallized from acetone, yielding the desired 2'3'-diacyl uridine derivative (adapted from Baker et al., *J. Med. Chem.* 22:273 (1979)).

Example VII: Preparation of $N^3 2',3,5'$Tetraacyl Uridine

The acylation of the secondary amine in the 3 position of the pyrimidine ring is accomplished by reacting 2',3',5'-triacyl uridine with 1.1 molar equivalents of the acid chloride of the desired acyl substituent in an aprotic solvent (such as ether, dioxane, chloroform, ethyl acetate, acetonitrile, pyridine, dimethylformamide and the like) in the presence of 1–5 molar equivalents of an organic base (especially aromatic amines such as pyridine, trialkylamines, or N,N-dialkylanilines) adapted from Fujii et al., U.S. Pat. No. 4,425,335). The acyl substituent on the secondary amine can be the same or different from those on the hydroxyl groups of the ribose moiety.

Example VIII: Preparation of 2',3',5'-Triacyl Cytidine

One gram of cytidine hydrochloride is dissolved in 10 ml of N,N-dimethylformamide. 3.1 molar equivalents of the acid chloride is added and the mixture is stirred overnight at room temperature. The reaction mixture is concentrated in vacuo to an oil, and triturated with 1.1 ethyl acetate: diethyl ester. The oil is then triturated with 1N sodium hydrogen carbonate. The crystalline solid is collected, washed with water, dried, and recrystallized (adapted from Gish et al., *J. Med. Chem.* 14:1159 (1971)).

Example IX: Preparation of 5'-Acyl Cytidine

One gram of cytidine hydrochloride is dissolved in 10 ml of N,N-dimethylformamide. 1.1 molar equivalents of the acid chloride of the desired acyl substituent is added, and the mixture is stirred overnight at room temperature. The reaction mixture is concentrated in vacuo to an oil, and triturated with 1:1 ethyl acetate: diethyl ether. The oil is then triturated with 1N sodium hydrogen carbonate. The crystalline solid is collected, washed with water, dried, and recrystallized (adapted from Gish et al., *J. Med. Chem.* 14:1159 (1971)).

Example X: Preparation of N⁴-Acyl Cytidine

The N⁴-amino group of cytidine is the best nucleophile among the amino and hydroxyl functionalities of cytidine. Selective N⁴-acylation can be accomplished by treating cytidine with appropriate acid anhydrides in pyridine or a mixture of pyridine and N,N-dimethylformamide. Specifically, 1 gram of cytidine is suspended in 80 ml of dry pyridine; 1.5 molar equivalents of desired acid anhydride is added, and the mixture is refluxed for 2 hours. The solvent is removed in vacuo, and the resulting white solid is recrystallized from ethanol.

Alternatively, cytidine (1 gram) is dissolved in a mixture comprising 70:30 pyridine:N,N-dimethylformamide. 1.5 molar equivalents of the acid anhydride of the desired acyl substituent is added, and the mixture is stirred overnight at room temperature, after which it is poured into water and stirred. The solvent is removed in vacuo to leave a white solid, which is extracted with diethy ether. The residue is recrystallized from ethanol (adapted from Sasaki et al., *Chem. Pharm. Bull* 15:894 (1967)).

An alternative procedure is to dissolve cytidine in a mixture of water and a water-miscible organic solvent (such as dioxane, acetone, acetonitrile, N,N-dimethylformamide, dimethylsulfoxide, tetrahydrofuran, etc.) and to treat that solution with about a twofold excess of an appropriate acid anhydride. For example, 1 gram of cytidine dissolved in 5 ml of water is mixed with 15 to 100 ml dioxane (more dioxane is needed for more lipophilic substituents), and 2 molar equivalents of the acid anhydride of the desired acyl substituent is added. The mixture is stirred for 5 hours at 80° C. (or 48 hours at room temperature), and then the solvent is removed in vacuo. The residue is washed with hexane or benzene, and recrystallized from ethanol or ethyl acetate (adapted from Akiyama et al., *Chem. Pharm. Bull.* 26:981 (1978).

Example XI: Preparation of N⁴,2',3',5'Tetraacyl Cytidine

Compounds in which the acyl substituent of the N⁴ amino group and the hydroxyl groups of the ribose ring of cytidine are the same (e.g., tetraacetyl cytidine) are prepared by dissolving or suspending cytidine in dry pyridine, adding at least 4 molar equivalents of the acid chloride or acid anhydride of the desired substituent, and stirring the mixture overnight at room temperature. The solvent is removed in vacuo and the residue is washed and recrystallized.

Having now fully described this invention, it will be appreciated by those skilled in the art that the same can be performed within a wide range of equivalent parameters of composition, conditions, and modes of administration without departing from the spirit or scope of the invention or any embodiment thereof.

What is claimed is:

1. A method of delivering exogenous uridine to the tissue of an animal, comprising the step of administering to said animal an acyl derivative of uridine, having the formula

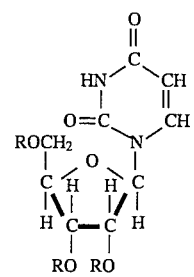

wherein R is H or an acyl group derived from a carboxylic acid selected from one or more of the group consisting of acetic acid, glycolic acid, pyruvic acid, lactic acid, enolpyruvic acid, an amino acid, a fatty acid, lipoic acid, pantothenic acid, succinic acid, fumaric acid, adipic acid, acetoacetic acid, p-aminobenzoic acid, betahydroxybutyric acid, orotic acid, and creatine, with the proviso that at least one R is not hydrogen, or the pharmaceutically acceptable salt thereof.

2. A method of delivering exogenous cytidine to the tissue of an animal, comprising the step of administering to said animal an acyl derivative of cytidine, having the formula

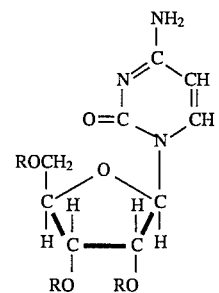

wherein R is H or an acyl group derived from a carboxylic acid selected from one or more of the group consisting of acetic acid glycolic acid, pyruvic acid, lactic acid, enolpyruvic acid, an amino acid, a fatty acid, lipoic acid, pantothenic acid, succinic acid, fumaric acid, adipic acid, acetoacetic acid, p-aminobenzoic acid, betahydroxybutyric acid, orotic acid, and creatine, with the proviso that at least one R is not hydrogen, or the pharmaceutically acceptable salt thereof.

3. A method of treating cardiac insufficiency comprising the step of administering to an animal in need of such treatment an acyl derivative of uridine in an amount to effect such treatment, having the formula

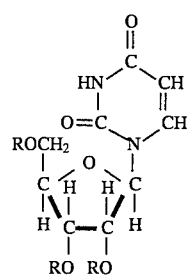

wherein R is H or an acyl group derived from a carboxylic acid selected from one or more of the group consisting of acetic acid, glycolic acid, pyruvic acid, lactic acid, enolpyruvic acid, an amino acid, a fatty acid, lipoic acid, pantothenic acid, succinic acid, fumaric acid, adipic acid, acetoacetic acid, p-aminobenzoic acid, betahydroxybutyric acid, orotic acid, and creatine, with the proviso that at least one R is not hydrogen, or the pharmaceutically acceptable salt thereof.

4. A method of treating myocardial infarction comprising the step of administering to an animal in need of such treatment an acyl derivative of uridine in an amount to effect such treatment, having the formula

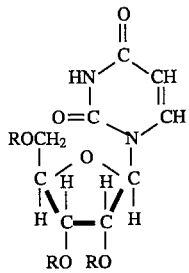
(I)

wherein R is H or an acyl group derived from a carboxylic add selected from one or more of the group consisting of acetic acid, glycolic acid, pyruvic acid, lactic acid, enolpyruvic acid, an amino acid, a fatty acid, lipoic add, pantothenic acid, succinic acid, fumaric acid, adipic acid, acetoacetic acid, p-aminobenzoic acid, betahydroxybutyric acid, orotic acid, and creatine, with the proviso that at least one R is not hydrogen, or the pharmaceutically acceptable salt thereof.

5. A method of treating cardiac insufficiency comprising the step of administering to an animal in need of such treatment an acyl derivative of cytidine in an amount to effect such treatment, having the formula

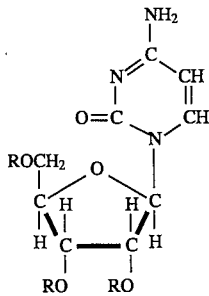
(III)

wherein R is H or an acyl group derived from a carboxylic acid selected from one or more of the group consisting of acetic acid, glycolic add, pyruvic add, lactic acid, enolpyruvic acid, an amino acid, a fatty acid, lipoic acid, pantothenic acid, succinic acid, fumaric acid, adipic acid, acetoacetic acid, p-aminobenzoic acid, betahydroxybutyric acid, orotic acid, and creatine, with the proviso that at least one R is not hydrogen, or the pharmaceutically acceptable salt thereof.

6. A method of treating myocardial infarction comprising the step of administering to an animal in need of such treatment an acyl derivative of cytidine in an amount to effect such treatment, having the formula

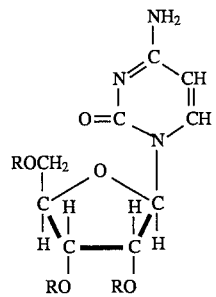
(III)

wherein R is H or an acyl group derived from a carboxylic acid selected from one or more of the group consisting of acetic acid, glycolic add, pyruvic acid, lactic acid, enolpyruvic acid, an amino acid, a fatty acid, lipoic acid, pantothenic acid, succinic acid, fumaric acid, adipic acid, acetoacetic acid, p-aminobenzoic acid, betahydroxybutyric acid, orotic acid, and creatine, with the proviso that at least one R is not hydrogen, or the pharmaceutically acceptable salt thereof.

7. A method as in claim 1 wherein said amino acid is selected from the group consisting of glycine, the L forms of alanine, valine, leucine, isoleucine, phenylalanine, tyrosine, cysteine, cystine, methionine, tryptophan, aspartic acid, glutamic acid, arginine, lysine, histidine, ornithine, and hydroxylysine.

8. A method as in claim 2 wherein said amino acid is selected from the group consisting of glycine, the L forms of alanine, valine, leucine, isoleucine, phenylalanine, tyrosine, cysteine, cystine, methionine, tryptophan, aspartic acid, glutantic acid, arginine, lysine, histidine, ornithine, and hydroxylysine.

9. A method as in claim 1 wherein said carboxylic acid is a fatty acid having 2–18 carbon atoms.

10. A method as in claim 2 wherein said carboxylic acid is a fatty acid having 2–18 carbon atoms.

11. A method as in claim 9 wherein said acyl derivative of uridine is administered orally.

12. A method as in claim 10 wherein said acyl derivative of cytidine is administered orally.

13. A method as in claim 3 wherein said carboxylic acid is a fatty acid having 2–8 carbon atoms.

14. A method as in claim 3 wherein said acyl derivative of uridine is administered orally.

15. A method as in claim 4 wherein said carboxylic acid is a fatty acid having 2–18 carbon atoms.

16. A method as in claim 4 wherein said acyl derivative of uridine is administered orally.

17. A method as in claim 5 wherein said carboxylic acid is a fatty acid having 2–18 carbon atoms.

18. A method as in claim 5 wherein said acyl derivative of cytidine is administered orally.

19. A method as in claim 6 wherein said carboxylic acid is a fatty acid having 2–18 carbon atoms.

20. A method as in claim 6 wherein said acyl derivative of cytidine is administered orally.

* * * * *